United States Patent
Chiniforooshan et al.

(10) Patent No.: US 9,851,338 B1
(45) Date of Patent: Dec. 26, 2017

(54) FIBER-OPTIC FLUORESCENCE SENSOR FOR HIGHLY SENSITIVE AND SPECIFIC DETECTION OF CHEMICAL HAZARDS

(71) Applicant: SPI—Security Protection International / Securite protection Internationale, Laval (CA)

(72) Inventors: Yasser Chiniforooshan, Ottawa (CA); Wojtek Bock, Ottawa (CA)

(73) Assignee: SPI—Security Protection International/Securite Protection Internationale, Laval (CA)

( * ) Notice: Subject to any disclaimer, the term of this patent is extended or adjusted under 35 U.S.C. 154(b) by 0 days.

(21) Appl. No.: 15/190,345

(22) Filed: Jun. 23, 2016

(51) Int. Cl.
  G02B 6/26 (2006.01)
  G01N 33/20 (2006.01)
  G02B 6/14 (2006.01)
  G02B 6/02 (2006.01)
  G01N 21/64 (2006.01)

(52) U.S. Cl.
  CPC ......... G01N 33/20 (2013.01); G01N 21/6404 (2013.01); G02B 6/0208 (2013.01); G02B 6/14 (2013.01); G01N 2021/6417 (2013.01); G01N 2021/6484 (2013.01)

(58) Field of Classification Search
  CPC ............... G01J 3/1895; G02B 6/02066; G02B 6/02095; G02B 6/29316; G02B 6/0208; G02B 6/14; G01N 33/20; G01N 21/6404; G01N 2021/6417; G01N 2021/6484
  See application file for complete search history.

(56) References Cited

U.S. PATENT DOCUMENTS

| | | | | |
|---|---|---|---|---|
| 5,253,037 A * | 10/1993 | Klainer | ................ | G01N 21/552 356/133 |
| 5,864,641 A * | 1/1999 | Murphy | ............... | G01N 21/774 250/227.14 |
| 6,021,240 A * | 2/2000 | Murphy | ............. | G01D 5/35377 250/227.14 |
| 7,327,908 B1 * | 2/2008 | Iazikov | .................... | G01D 5/38 385/12 |
| 8,351,029 B2 * | 1/2013 | Nishikawa | ......... | G01D 5/35383 356/128 |
| 8,805,136 B2 * | 8/2014 | El-Sherif | ........... | G02B 6/02066 359/240 |
| 2007/0075225 A1* | 4/2007 | Xia | .................... | G01N 21/7703 250/227.14 |
| 2015/0055133 A1* | 2/2015 | Egalon | ................ | G01F 23/2927 356/402 |

* cited by examiner

Primary Examiner — Ellen Kim
(74) Attorney, Agent, or Firm — Benoit & Cote Inc.

(57) ABSTRACT

There is described a fiber-optic sensor for measuring a light signal from a fluorescible sample comprising heavy metal ions, for example. The fiber-optic sensor comprises an optical fiber having a side surface by which the light signal from the fluorescible sample is inputted. The optical fiber is corrugated to form at least two gratings on the side surface of the optical fiber. Each grating comprises periodically longitudinally spaced-apart valleys on the surface of the optical fiber, and is longitudinally spaced apart from any other grating of the at least two gratings.

24 Claims, 20 Drawing Sheets

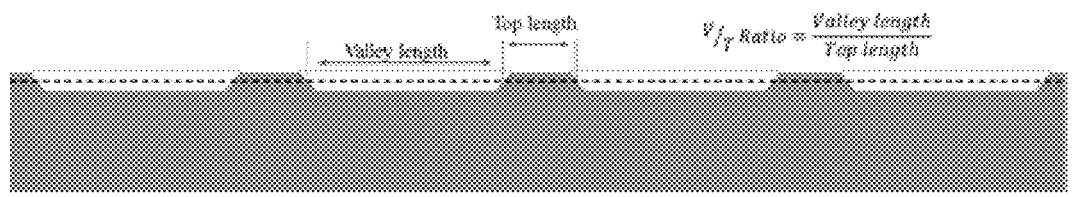
FIGURE 8
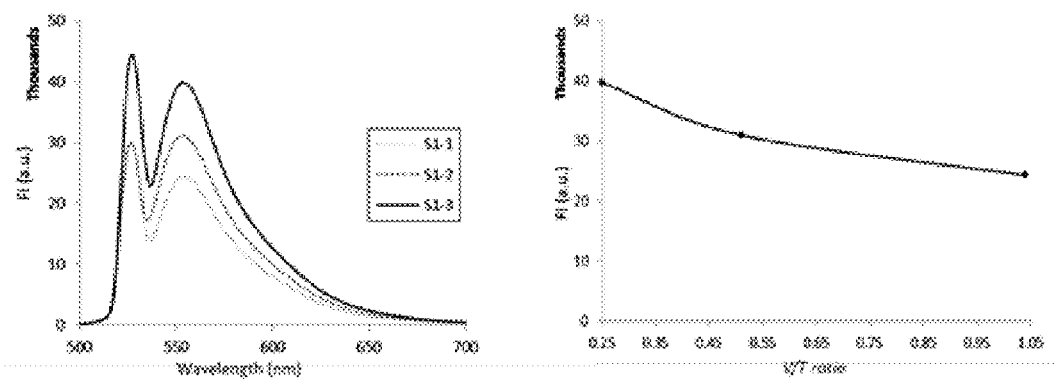
FIGURE 9A
FIGURE 9B
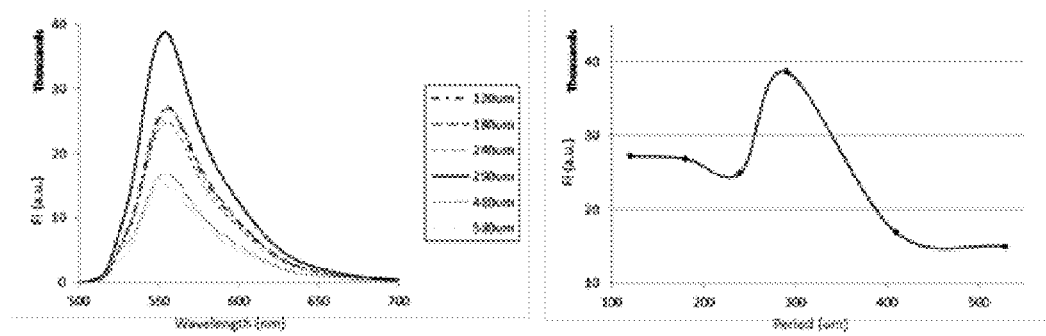
FIGURE 10A
FIGURE 10B
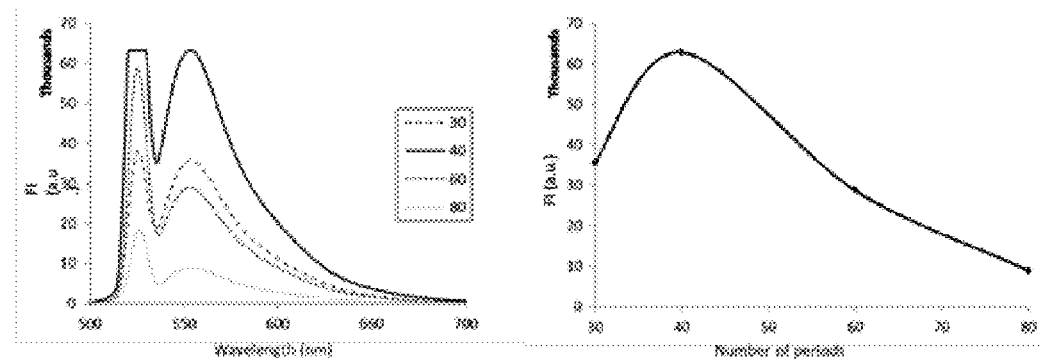
FIGURE 11A
FIGURE 11B

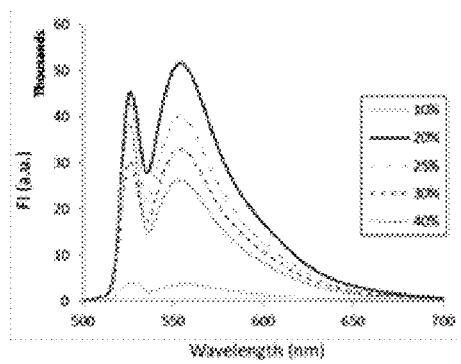
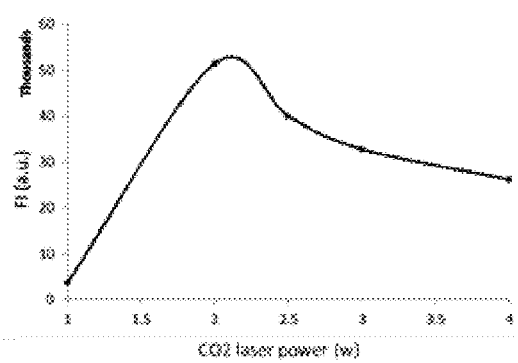
FIGURE 12A  FIGURE 12B
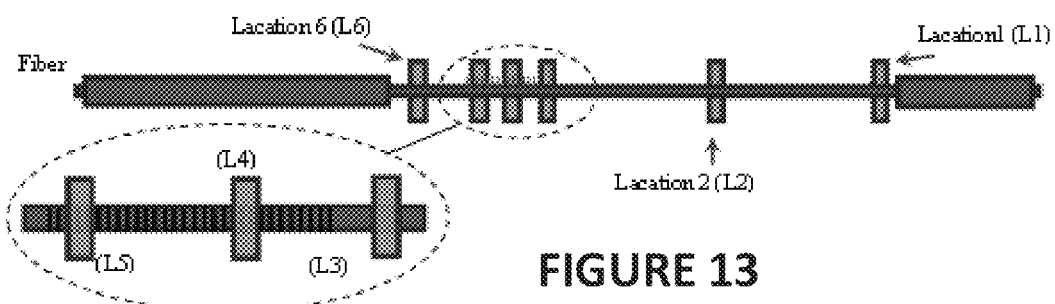
FIGURE 13
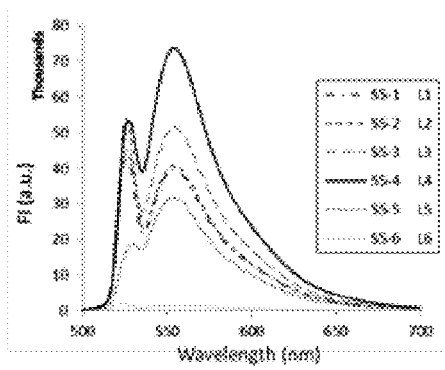
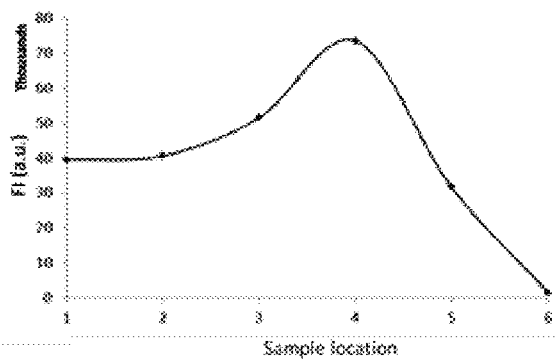
FIGURE 14A  FIGURE 14B

FIBER-OPTIC FLUORESCENCE SENSOR FOR HIGHLY SENSITIVE AND SPECIFIC DETECTION OF CHEMICAL HAZARDS

BACKGROUND (a) Field

The subject matter disclosed generally relates to fiber optic sensors. More specifically, it relates to sensors for the measurement of chemical concentrations of chemical hazards.

(b) Related Prior Art

There exist various sensors for detecting various chemical components.

A critical aspect of chemical compound detection is the measurement of heavy metal ions in drinking water. Heavy metal ions such as lead ions or copper ions can have deleterious effects on human health even at low concentrations. Since everyone can be affected, solutions for detection of these harmful substances should be widespread and therefore cheap to fabricate and easy to operate.

Such sensors should also have sufficient sensitivity since the substances at issue can be harmful even at very low concentrations that can be hard to detect without sophisticated equipment.

SUMMARY

There are disclosed fiber-optic sensors based on fluorescence detection, especially for chemical or biological sensing applications. More precisely, there are described corrugated fiber gratings (CFGs) imprinted on the core of "large-core" (highly multi-mode) optical fibers. This type of the fiber sensor is used as an intrinsic bulk sensitive fluorescence sensor. This architecture gives the capability of depth detection of fluorescence as well as of multi-target fluorescence detection on a single fiber. The receptor, which has a chemical affinity to the target, is tagged with fluorophore dyes. Photoinduced electron transfer (PET) technique is used for fluorescence quenching or turn-on. The change in fluorescence intensity is detected by the corrugated fiber grating sensor described herein. Moreover, the sensor is utilized to detect several chemical targets critical in monitoring the environmental safety.

Heavy metal ions can be a source of dangerous contamination of drinking water or in industrial waste water, and as a result need to be detected in trace amounts. The fiber-optic fluorescence sensors described herein can be used to detect low concentrations (i.e., traces) of heavy metal ions in aqueous environment, $Cu^{2+}$ and $Pb^{2+}$ for example, or any other metallic ion to be measured such as $Co^{2+}$, $Ni^{2+}$, $Zn^{2+}$, $Cd^{2+}$, $Hg^{2+}$, $Ca^{2+}$, $Mg^{2+}$, $Mn^{2+}$, $Fe^{3+}$, $K^+$, etc. The chemical probe is designed to have high specificity for the targets and to radiate fluorescence by attaching to the targets based on the PET mechanism. The fiber-optic fluorescence sensor is also optimized for the fluorescence radiation range.

For example, using the CFG based sensor the limit of detection for $Pb^{2+}$ ions is as low as 1.94 ppb, which is far below the action level of 15 ppb established by the EPA for drinking water. The ability of multi-target and depth detection of the CFG based sensor is also shown by some experiments.

This sensor is suitable for a wide range detection of fluorescence radiation, which can be used for various chemical or biological targets. The fiber sensor can be optimized for a specific working wavelength, which is usually defined by the properties of the chosen chemical probe, and therefore can be utilized for detection of many different targets. This makes the sensor platform potentially extremely cost-effective.

According to an aspect of the invention, there is provided a fiber-optic sensor for measuring a light signal from a fluorescible sample, the fiber-optic sensor comprising:

an optical fiber having a side surface by which the light signal from the fluorescible sample is inputted, the optical fiber being corrugated to form at least two gratings on the side surface of the optical fiber, each grating: comprising periodically longitudinally spaced-apart valleys on the surface of the optical fiber; and being longitudinally spaced apart from any other grating of the at least two gratings.

According to an embodiment, the optical fiber comprises an un-cladded segment, the gratings being imprinted on the core of the un-cladded segment.

According to an embodiment, the optical fiber is a large-core optical fiber thereby being highly multi-mode.

According to an embodiment, each grating is configured to couple high-order modes to low-order modes.

According to an embodiment, the light signal from the fluorescible sample comprises leaky modes, the grating converting the leaky modes into bound core modes that can propagate within a cladded segment of the optical fiber for eventual detection at a detection device provided at an end of the optical fiber.

According to an embodiment, each grating is characterized by parameters comprising: a period between its valleys, a depth of its valleys and a length of its valleys; the parameters being adjusted for optimal mode-conversion of a given wavelength according to coupled-mode equations.

According to an embodiment, the given wavelength for which mode conversion is optimized is about a peak wavelength of fluorescence of a heavy metal ion in a fluorophore solution.

According to an embodiment, the heavy metal ion comprises $Pb^{2+}$, $Cu^{2+}$, and combinations thereof.

According to an embodiment, the heavy metal ion comprises $Pb^{2+}$, $Cu^{2+}$, $Co^{2+}$, $Ni^{2+}$, $Zn^{2+}$, $Cd^{2+}$, $Hg^{2+}$, $Ca^{2+}$, $Mg^{2+}$, $Mn^{2+}$, $Fe^{3+}$, $K^+$, and combinations thereof.

According to an embodiment, wherein each one of the at least two gratings has an azimuth about which its valleys are imprinted.

According to an embodiment, the at least two gratings is two gratings.

According to an embodiment, the azimuths of the two gratings are substantially the same.

According to an embodiment, the azimuths of the two gratings are substantially different.

According to an embodiment, the azimuths of the two gratings differ from about 90°.

According to another aspect of the invention, there is provided a method of fabricating a fiber-optic sensor, the method comprising: un-cladding a segment of an optical fiber to uncover a surface on a side thereof; providing an energetic beam; imprinting a plurality of gratings on the surface of the optical fiber, comprising imprinting a plurality of valley on the surface of the optical fiber using the energetic beam; wherein between each imprinting of a valley, a relative displacement along a longitudinal axis of the optical fiber is performed between the optical fiber and the energetic beam, such that each valley is periodically longitudinally spaced-apart from any other valley belonging to a given grating; wherein between each imprinting of a grating, a relative displacement along a longitudinal axis of the optical fiber is performed between the optical fiber and the energetic beam, such that each grating is longitudinally spaced-apart from any other grating.

According to an embodiment, there is further provided, between each imprinting of a grating, rotating the optical fiber with respect to its longitudinal axis, such that each grating is provided at an azimuth different from that of any other grating.

According to an embodiment, the plurality of gratings comprises imprinting two gratings.

According to an embodiment, rotating the optical fiber between each imprinting of a grating comprises rotating the optical fiber by about 90° with respect to its longitudinal axis between the imprinting of the two gratings.

According to an embodiment, the energetic beam is a laser beam.

According to an embodiment, the energetic beam is an infrared radiation.

According to an embodiment, the energetic beam is a high energy radiation, the method further comprising applying weight on the optical while providing the high energy radiation.

According to an embodiment, imprinting each grating comprises imprinting a grating characterized by parameters comprising: a period between its valleys, a depth of its valleys and a length of its valleys; the parameters being adjusted for optimal mode-conversion of a given wavelength according to coupled-mode equations.

According to an embodiment, the given wavelength for which mode conversion is optimized is a peak wavelength of fluorescence of a heavy metal ion in a fluorophore solution.

According to an embodiment, the heavy metal ion comprises $Pb^{2+}$, $Cu^{2+}$, and combinations thereof.

According to an embodiment, the heavy metal ion comprises $Pb^{2+}$, $Cu^{2+}$, $Co^{2+}$, $Ni^{2+}$, $Zn^{2+}$, $Cd^{2+}$, $Hg^{2+}$, $Ca^{2+}$, $Mg^{2+}$, $Mn^{2+}$, $Fe^{3+}$, $K^+$, and combinations thereof.

Definitions

Optical fiber: The optical fiber is used in its ordinary meaning in the art. It is a long cylinder-shape piece of glass through which light can propagate. For optimal propagation, it is usually required that the travelling light belongs to the operatable working range of wavelengths of the optical fiber. The optical fiber comprises a core at the center of the cylinder and a clad provided around the core which normally has a different index of refraction that the core to allow the light to propagate within the fiber instead of escaping the fiber. The clad can be removed so that portions of the optical fiber can be un-cladded. The core is then immediately surrounded by air or water, for example.

Multi-mode: In an optical fiber, a light beam can be decomposed into fundamental modes of propagation, in a way analogous to a signal decomposed into sines of different frequencies. If the optical fiber has a narrow core, only one mode can propagate (i.e., it is single-mode). If the core is large enough, various modes can propagate within the fiber, i.e., the fiber is thereby a multi-mode fiber. Some modes may have properties that do not allow them to propagate into the fiber (evanescent or leaky modes), while others can propagate without significant loss (bound-core modes). Perturbations in or on the optical fiber break the perfect circular geometry and allows mode conversion of the light signal, i.e., energy that is propagating in a mode can be transferred to another mode.

Grating: A grating is a pattern of varying index of refraction or of varying geometry imprinted in an optical fiber or on its surface. This perturbation pattern is often periodical. The grating causes various types of effects on the light signal (selective reflection, mode conversion, etc.), which selectively apply to specific wavelength ranges depending on the properties of the grating.

Fluorophore: The fluorophore is a substance (it can be a solution such as an aqueous solution) that emits fluorescent light in some circumstances such as when it receives higher-energy radiations. The fluorescence spectrum can be modified if other substances, such as ions, are present in the fluorophore. The fluorophore is the signaling species, i.e. it acts as a signal transducer that converts the information (presence of an analyte) into an optical signal expressed as the changes in the photophysical characteristics of the fluorophore.

Sample: The sample is the fluorophore which contains an analyte therein (e.g., heavy metal ions). The concentration of analyte in the sample needs to be assessed. The sample is qualified as fluorescible, i.e., it can fluoresce in the right circumstances, usually upon irradiation of the sample by higher-energy radiation.

BRIEF DESCRIPTION OF THE DRAWINGS

Further features and advantages of the present disclosure will become apparent from the following detailed description, taken in combination with the appended drawings, in which:

FIG. 8 is a side view of the fiber probe, the CFG structure and the definition of V/T Ratio, according to an embodiment of the present invention;

FIGS. 9A-9B are graphs illustrating a fluorescence signal captured by fiber probes with different V/T Ratio and the fluorescence intensity at 555 nm versus V/T Ratio, according to an embodiment of the present invention;

FIGS. 10A-10B are graphs illustrating a fluorescence signal captured by fiber probes with different period size and the fluorescence intensity at 555 nm versus period size, according to an embodiment of the present invention;

FIGS. 11A-11B are graphs illustrating a fluorescence signal captured by fiber probes with different number of periods and the fluorescence intensity at 555 nm versus number of periods, according to an embodiment of the present invention;

FIGS. 12A-12B are graphs illustrating a fluorescence signal captured by the fiber probes with different $CO_2$ laser power used for CFG writing and the fluorescence intensity at 555 nm versus power of $CO_2$ laser, according to an embodiment of the present invention;

FIG. 13 is a side view illustrating definitions of L1-L6, the different locations of the SUT, according to an embodiment of the present invention;

FIGS. 14A-14B are graphs illustrating a fluorescence signal captured by the fiber probes when the SUT is placed in different locations and the fluorescence intensity is at 555 nm versus the locations of the SUT, according to an embodiment of the present invention;

It will be noted that throughout the appended drawings, like features are identified by like reference numerals.

DETAILED DESCRIPTION

There is described herein a corrugated fiber grating optical fiber used as a sensor for measuring a light signal from a fluorescible sample.

Intrinsic Developed Fiber Sensor: Corrugated Fiber Grating

The corrugated fiber grating optical fiber fluorescence configuration has been determined as being efficient and very well adapted for the considered applications. It uses the side-wall of the fiber and a mechanism to couple refracting rays to the bound rays. A type of grating called corrugated fiber grating (CFG) is introduced for the repeatability and improvement of the sensor.

Figure 1:
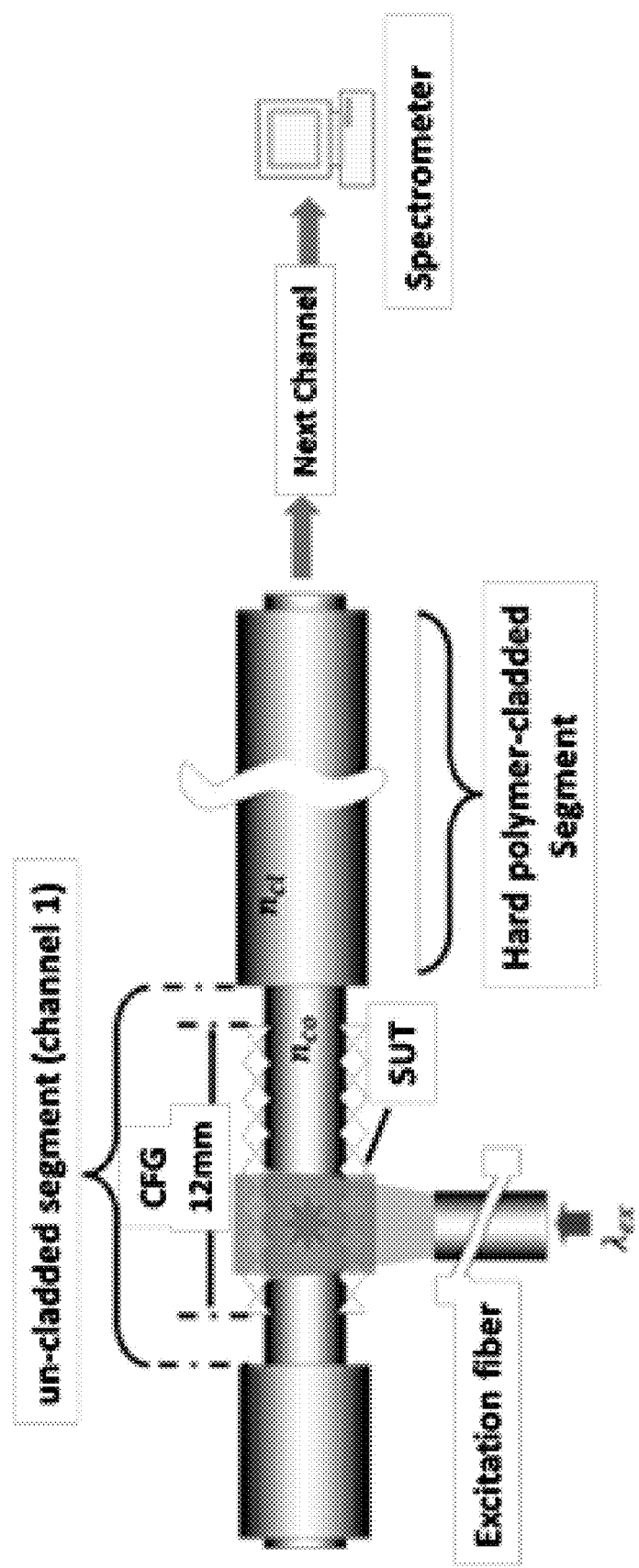
FIG. 1 is a side view illustrating a fiber optic fluorescence sensor with its four segments: SUT, Air-cladded, Corrugated fiber grating and hard polymer-cladded segments, according to an embodiment of the present invention.

The proposed multi-segment fluorescence fiber probe is shown in FIG. 1. Comparing to traditional fiber-optic fluorescence probes, there are several differences which distinguish this probe as a bulk fluorescence probe that uses the side-wall of the fiber rather than its end-face. In this probe a small volume of the sample is needed to take measurements. Unlike the tapered or evanescent-wave fluorescence probes, the segment used for detection could be as short as 15 mm and the sample under the test can cover just few millimeters of that segment with a quantity as low as few microliters. This short detection channel has many advantages, such as being a rigid and a multi-target sensor.

The proposed sensor is comprised of four segments, liquid-cladded or sample under test (SUT), air-cladded, corrugated fiber grating (CFG), and hard polymer-cladded segments as shown in FIG. 1. The fluorescence is released in the SUT segment, and then some of the fluorescent light intensity reaches the air-cladded segment and propagates to face the CFG that couples the higher-order modes to lower-order modes to transform the leaky modes in the hard polymer-cladded segment into the bound modes. Without CFG there would be no considerable guided power that can propagate in the hard polymer-cladded segment and just a very small portion of the leaky modes would be coupled to the bound modes by the evanescent wave tail. By designing an optimized CFG those leaky modes could be efficiently coupled to the bound modes.

A mode in an optical waveguide, an optical fiber in this case, is a set of electromagnetic waves which carry the energy along the fiber. The electromagnetic field distributions can be calculated using the Maxwell's equations and applying the electric and magnetic boundary conditions at the interfaces. By solving those equations the two main classes of modes called bound and leaky modes can be found. The loss for the bound modes is small, therefore they can propagate all along the fiber while the leaky modes face a big loss and radiate out of the fiber within a distance. A finite number of bound modes can propagate inside the fiber.

Figure 2:
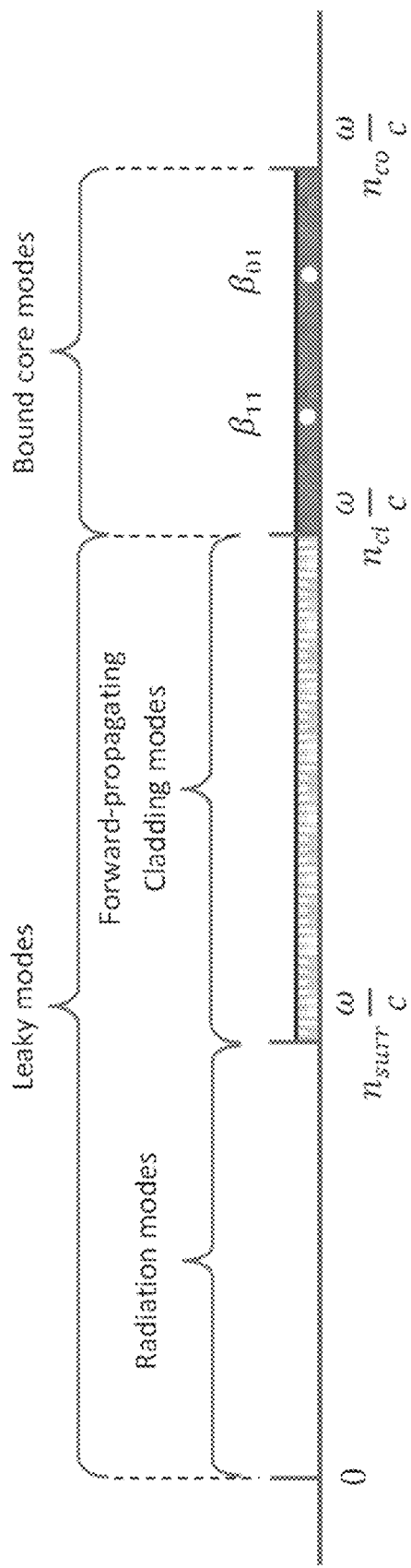
FIG. 2 is a graph illustrating the definitions of the leaky, radiation, cladding and bound modes in β-plot, according to an embodiment of the present invention.

Each mode has a propagation constant β that is related to the mode's effective index by the expression $\beta = \omega n/c$, where ω, n and c are angular frequency, effective index, and the free space light speed, respectively. It can be shown that the effective index of the core modes that are bound inside the core is confined between core and cladding refractive index, $n_{co} > n_{eff\text{-}co} > n_{cl}$. The effective index of the cladding modes which propagate in the cladding is also confined between the cladding and surrounding refractive index, $n_{cl} > n_{eff\text{-}cl} > n_{surr}$. However, the loss for the cladding modes is high and they cannot exist after a short propagation. A pictorial way to show the effective index of the different modes is a β-plot which represents the modal propagation constants in terms of the angular frequency FIG. 2.

According to FIG. 1, an exemplary large-core fiber with the core/cladding diameter and refractive indices of 400/430 μm and 1.46/1.41 is used for the probe. The surrounding sample also has a refractive index of 1.33. A fiber with these dimensions and refractive indices supports a large number of bound modes in each segment. This is why such a large-core fiber would be used for the probe. The number of bound modes supported by the fiber can be calculated using the V-number of the fiber:

$$M_{bm} = Int\left(\frac{V^2}{2}\right), V = \frac{2\pi\rho}{\lambda}$$

where ρ is the core radius and λ is the free space wavelength. With simple calculations, it can be shown that the numbers of bound modes supported by the probe in liquid-cladded, air-cladded, and hard polymer-cladded segments are 928884, 2901640, and 368082, respectively. When a fiber supports such a large number of modes, the effective indices of modes can be considered as continuous numbers between core and cladding refractive indices. This approximation is valid since the difference between two mode's effective indices is in the order of $10^{-7}$ if the free space wavelength is 555 nm. Considering this approximation it can be shown how the probe works using a β-plot for each segment.

Fluorescence Modal Propagation and Coupling

Figure 3:
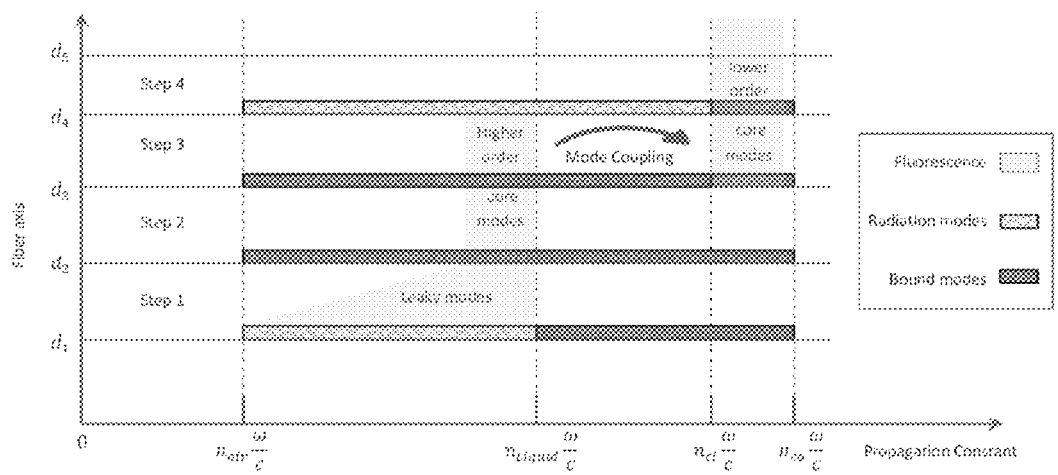
FIG. 3 is a graph illustrating a β-plot in different segments of the proposed fiber-optic fluorescence sensor, according to an embodiment of the present invention.

There are three steps in propagation of the fluorescence light inside the probe. Step 1 is the excitation and propagation of the fluorescence in the liquid-segment. Step 2 is the propagation of remaining fluorescence in the air-cladded segment. Step 3 is the coupling of higher order core modes to the lower order ones in air-cladded segment and finally, step 4 is the propagation of the fluorescence in the hard polymer-cladded segment towards the detector, i.e., the optical spectrometer, provided at an end of the optical fiber. These steps are shown in FIG. 3 as four related β-plots. The radiation and bound modes as well as the fluorescence propagation areas in each segment are shown using different textures.

As shown in FIG. 3, the fluorescence that is excited in the liquid-cladded segment ($d_2 > d \geq d_1$) propagates in the form of cladding or radiation modes. Therefore, a part of the fluorescence would be lost depending on the length of the liquid-cladded segment. For this reason the $d_2$–$d_1$ should neither be too large to absorb all of the fluorescence nor too small so that the fluorescence would be low. An optimum length that has been used for liquid-cladded segment is 2 mm. Since the remaining fluorescence can be considered as higher-order core modes in the air-cladded segment $d_3 > d \geq d_2$, it propagates without considerable loss in this segment towards the CFG. As shown in FIG. 3 the propagation constants of the higher-order core modes before the CFG are not suitable for propagation in the hard polymer-cladded segment if they do not couple to the lower-order core modes. Thus the CFG plays a critical role in this probe by coupling the higher-order to the lower-order core modes in the air-cladded segment $d_4 > d \geq d_3$.

By optimizing the parameters of the CFG it was possible to couple as much intensity as possible to the modes that are able to propagate without loss in the hard polymer-cladded segment towards the next channel $d \geq d_5$. The next channel also could be designed like the first channel considering what type of the target would be detected in which frequency range.

In such a highly multi-mode fiber, power can easily be transferred between two or more modes by small disturbances or irregularities in the fiber. In transferring data via fiber in optical communications, any coupling between the modes should be avoided because it would cause intermodal dispersion, resulting in attenuation and a decrease in the data rate. To the contrary, other useful devices such as sensors can be designed and fabricated by using this mode coupling. To control the coupling of the power between modes in a fiber the perturbation can be made periodic by bending or by modifying the refractive index or shape of the core or of the cladding. Following the method presented by Taylor and Yariv in 1974, the coupled mode equations are as follows, $$\frac{dA_1(z)}{dz} = \kappa_{12}A_2(z)e^{-j\Delta z}, \frac{dA_2(z)}{dz} = \kappa_{12}A_1(z)e^{+j\Delta z}$$

where $\kappa_{12}$ and $\kappa_{12}$ are cross-coupling coefficients that dictate the power exchanges between the two modes. $A_1(z)$ and $A_2(z)$ are complex normalized amplitudes in a lossless unperturbed fiber. In these equations Δ is the phase mismatch between the propagation modes. In the presence of a perturbation of period Λ it is modified to $$\Delta = \beta_1 - \beta_2 - \frac{2\pi m}{\Lambda}.$$

If the power transfers synchronously between two modes, the phase mismatch should ideally be zero. Thus the result is what is commonly termed the phase-matching condition between two modes, $$\Delta\beta = \beta_1 - \beta_2 = \frac{2\pi m}{\Lambda}.$$

The optical probe that uses the CFG can be modeled using the coupled-mode theory. Using the four last equations, it can be shown that for a certain operation wavelength there is a certain period that can be used for coupling of the power between two modes with the propagation constants of $\beta_1$ and $\beta_2$. However a highly multi-mode fiber can support a power exchange between desired ranges of propagation constants if it is perturbed by certain periodic irregularities such as the changes in the core diameter.

By using the assumption of continuous variation of the effective indices of the core modes in the large core fiber, it can be shown that the bandwidth of the coupler in this probe is wider than the fluorescence signal width. Therefore, the whole fluorescent intensity can be coupled from the higher order core modes to the lower order modes in the air-cladded segment.

Figure 4:
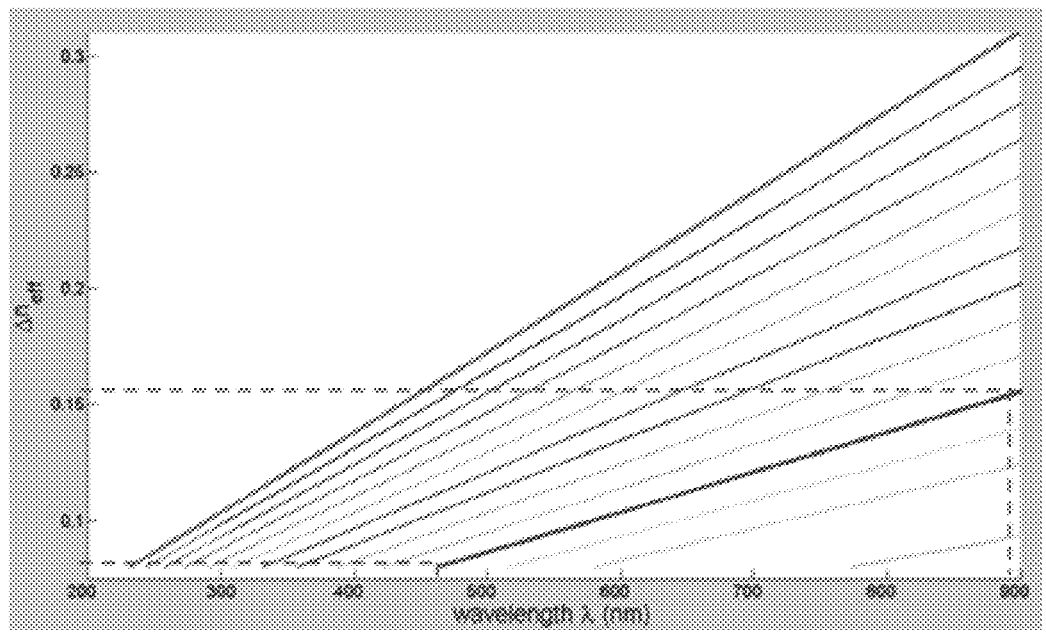
FIG. 4 is a graph illustrating the effective index difference of bound modes versus wavelength for the different orders of phase-matching in a periodic perturbation with a pitch size of 290 μm, according to an embodiment of the present invention.

From the phase-matching condition, the plot $\Delta n_{eff}$ versus $\lambda$ can be produced. In FIG. 4 the effective index differences of the two modes versus wavelength of operation are plotted. Different colors represent the different order of matching between the two modes.

As mentioned before, it can be assumed that the effective indices of the excited fluorescence in the liquid-cladded segment (step 1) are spread continuously between $n_{liquid}$ and $n_{air}$. However the power carried by the modes close to $n_{liquid}$ is higher since the farther the effective index is from $n_{liquid}$, the higher the attenuation of that mode. The excited fluorescence should be coupled to the guided modes of the hard polymer-cladded segment by the corrugated fiber grating. Those guided modes have effective indices spread almost continuously between $n_{core}$ and $n_{cladding}$. Thus the possible difference of effective indices between the original fluorescence and the coupled power could range from 0.08 up to 0.46. Using the above assumptions it is shown in FIG. 4 that for the higher-order phase-matching condition (between blue and red graphs) the bandwidth of the coupler at least covers the visible range from 400 nm to 900 nm. The continuous rather than the discrete propagation constants of the modes supported by this large-core fiber cause the wide-band coupling in this probe. Unlike some applications in optical communications and optical fiber sensing, this wide-band coupling is an advantage of the probe for fluorescence sensing as the fluorescence signals are commonly spectrally wide.

Fabrication Procedure

The corrugated fiber grating can be fabricated using a $CO_2$ laser beam. It can advantageously be optimized by selecting grating parameters (e.g. period, length, depth) for a specific fluorescence wavelength. The grating can be fabricated on the fiber side-wall by exposing it to a low energy IR radiation that would change the refractive index in both core and cladding.

Figure 5:
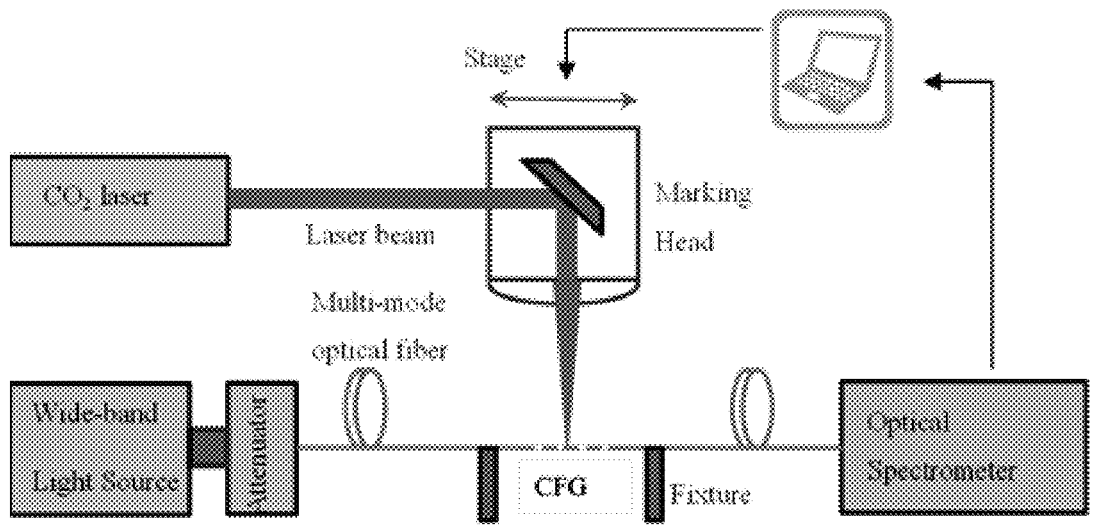
FIG. 5 is a diagram illustrating a corrugated fiber grating fabrication setup using a high power $CO_2$ laser, according to an embodiment of the present invention.
Figure 6:
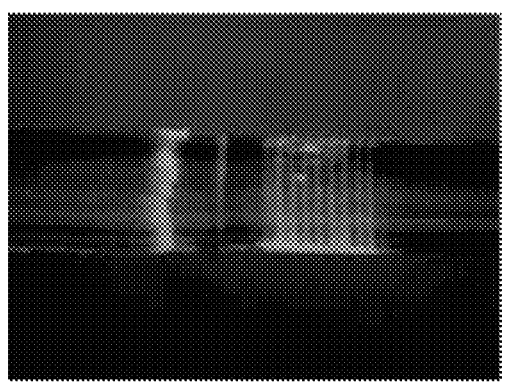
FIGS. 6-7 are pictures illustrating a CFG on a multi-mode fiber, according to an embodiment in which the CFG comprises lines separated by 50 μm with the depth of about 10 μm of the present invention.
Figure 7:
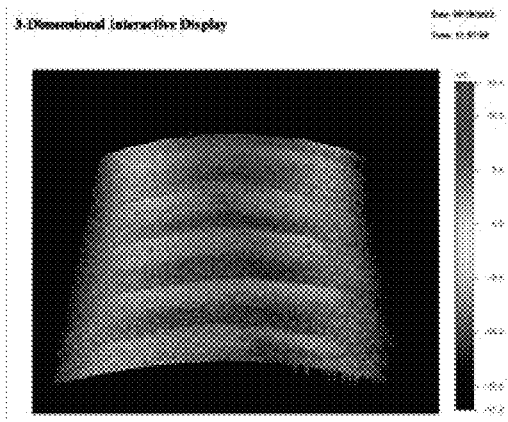

Another way is to project the higher radiation energy to corrugate the fiber side-wall. Corrugated fiber gratings (CFGs) are strong gratings, with few periods resulting in coupling between the modes being strong. Fabrication of these periods can be done by moving a laser beam along the fiber or moving the fiber under a fixed laser beam and applying some weight to the fiber. FIG. 5 shows the setup to fabricate a CFG on a multi-mode fiber. FIGS. 6-7 show a resulting sample of CFG fabricated on the side-wall of a multimode fiber.

To set all the parameters for more efficient fluorescence collection, a standard fluorescent solution is used. This solution is a Rhodamine 6G with concentration of 10.3 µg/ml in water. Since the chemical fluorescence probes usually have very low quantum yield ($\phi$), the parameters of the CFG should be optimized to increase the sensitivity of the optical fiber fluorescence sensor. These parameters can be listed as below:

Non-Equal Grating Pattern

Using $CO_2$ laser one can imprint an array of lines perpendicular to the fiber axis. Such a pattern generated a CFG along the fiber. As it is shown in FIG. 8 each line in this array had a thickness appropriate for generating a wide valley when it is projected on the fiber. The minimum thickness of the lines defined by the beam spot size at the focal point differed by the adjustments of $CO_2$ focus system. The equality or non-equality of the lengths of the valleys and tops lengths make different structures. By controlling the thickness of the lines one can make a variety of different optical probes with their specific valley-to-top length ratio.

FIG. 8 shows how one can control the different parameters to fabricate different patterns on the fiber. To compare the different grating patterns for the structure, perturbations were made with different valley to top length ratios (V/T Ratio), all other parameters being fixed, as listed in the table 1.

TABLE 1

The fabrication conditions of fiber probes with different V/T Ratio.

|  | V/T Ratio, Valley to Top length ratio | P, Period size (µm) | N, No. of periods | I, $CO_2$ power (total 10 W) | L, Sample Location |
|---|---|---|---|---|---|
| S1-1 | 1.04 | 290 | 20 | 30% | L1 |
| S1-2 | 0.51 | 290 | 20 | 30% | L1 |
| S1-3 | 0.25 | 290 | 20 | 30% | L1 |

Using the standard fluorescence solution, R6G (10.3 µg/ml in water), which is as a fluorophore solution, the collection efficiency of the optical probes with S1-1, S1-2 and S1-3 grating can be compared. FIGS. 9A-9B shows the fluorescent signal received and the intensity captured by each probe at peak emission wavelength (555 nm), respectively.

According to the experimental results in FIGS. 9A-9B, the optical probe had the best performance when the valley length was minimum. The valley length was defined by the minimum spot size of the laser beam at focal point. The smallest spot size of the beam is 116 µm which could be achieved by the lens with 80 mm of focal length.

Period Size (P)

According to the coupled mode theory, any perturbation on a fiber can couple or mix modes to each other. If there is a periodic perturbation then the coupling of a specific class of modes to another particular class of modes is possible. The period size plays a very important role in defining the specific modes that can be coupled. As mentioned in the previous sections, the CFG that was made on the fiber was asymmetric and could excite the asymmetric modes. The analytical calculations of those modes are very complicated since there are millions of symmetric modes and asymmetric ones. To achieve the best period size there were fabricated optical probes with different period sizes. In this step the size was optimized in the visible range. The characterization parameters of the different probes are listed in table 2.

TABLE 2

The fabrication conditions of fiber probes with different period size.

|  | V/T Ratio, Valley to Top width ratio | P, Period size (µm) | N, No. of periods | I, $CO_2$ power (total 10 w) | L, Sample Location |
|---|---|---|---|---|---|
| S2-1 | 0.25 | 120 | 20 | 30% | L1 |
| S2-2 | 0.25 | 180 | 20 | 30% | L1 |
| S2-3 | 0.25 | 240 | 20 | 30% | L1 |
| S2-4 | 0.25 | 290 | 20 | 30% | L1 |
| S2-5 | 0.25 | 410 | 20 | 30% | L1 |
| S2-6 | 0.25 | 530 | 20 | 30% | L1 |

FIGS. 10A-10B is a comparison of the efficiency of the probes with different period sizes. Same as before, the R6G fluorescence was used to test the collection capability of probes in the visible range with a center wavelength of 555 nm.

By changing the period, it is concluded that there is a specific period in which the coupling of radiation modes to the core modes in certain wavelength range would be maximized. FIGS. 10A-10B show the experimental data in which the optimized period was 290 μm, for the test configuration.

Number of Periods (N)

The number of periods in a periodic structure defines the percentage of coupling between the two classes of modes. To achieve the highest collection efficiency there is an optimized number of periods that should be imprinted on the fiber. By making the different number of periods and testing them with the standard R6G fluorophore solution it was possible to find the optimized number. Table 3 shows the parameters of the optical probes.

TABLE 3

The fabrication conditions of fiber probes with different number of periods.

| | V/T Ratio, Valley to Top width ratio | P, Period size (μm) | N, No. of periods | I, $CO_2$ power (total 10 w) | L, Sample Location |
|---|---|---|---|---|---|
| S3-1 | 0.25 | 290 | 30 | 30% | L1 |
| S3-2 | 0.25 | 290 | 40 | 30% | L1 |
| S3-3 | 0.25 | 290 | 60 | 30% | L1 |
| S3-4 | 0.25 | 290 | 80 | 30% | L1 |

FIGS. 11A-11B shows the optimized number of periods for the fluorescence in the range of visible light.

Depth of the Periods (I)

The depth of the grooves which are made by projecting the laser power to the fiber also affects the strength of the coupling. Since the excited fluorescence was placed around the fiber, the intensity is distributed mostly around the edge of the fiber. Very deep grooves are not as good as shallower ones since they affect lower order core modes as well. On the other hand, very shallow grooves also are not able to completely affect those higher-order modes. There is an optimized depth of grooves that can affect all the intensity of the higher order modes and at the same time, not affect the coupled modes of the lower orders. There is a relation between the depth of the periods and the power of the $CO_2$ laser used to make a grating. To find out the best depth, there were made different periods with the parameters as listed in table 4.

TABLE 4

The fabrication conditions of fiber probes with different CO2 power.

| | V/T Ratio, Valley to Top width ratio | P, Period size (μm) | N, No. of periods | I, $CO_2$ power (total 10 w) | L, Sample Location |
|---|---|---|---|---|---|
| S4-1 | 0.25 | 290 | 40 | 10% | L1 |
| S4-2 | 0.25 | 290 | 40 | 20% | L1 |
| S4-3 | 0.25 | 290 | 40 | 25% | L1 |
| S4-4 | 0.25 | 290 | 40 | 30% | L1 |
| S4-5 | 0.25 | 290 | 40 | 40% | L1 |

Below there are experimental results of different probes used for fluorescence collection from the standard R6G solution. Again the original signal received at the spectrometer and the intensity at emission wavelength (555 nm) in terms of the CO2 power are shown in FIGS. 12A-12B.

FIGS. 12A-12B show that the best power of the CO2 laser for imprinting the periods on the surface of the fiber was about 20 percent of the total power. The average total power of the laser is 10 W, therefore the optimized power would be about 2 W to achieve the most efficient gratings.

Sample Location (L)

There was an air-cladded segment between the sample and CFG and the fluorescent light propagated in this segment in the form of very high-order core modes. The sample location on the fiber relative to the CFG can vary and thereby affect the coupling. To compare the influence of the location on the signal strength the sample was put in different locations (FIG. 13).

By changing the location of the sample and by comparing the received signal one can conclude which location is the best. The table 5 shows the parameters of the different probes.

TABLE 5

The fabrication conditions of fiber probes with different location of the SUT.

| | V/T Ratio, Valley to Top width ratio | P, Period size (μm) | N, No. of periods | I, $CO_2$ power (total 10 w) | L, Sample Location |
|---|---|---|---|---|---|
| S5-1 | 0.25 | 290 | 40 | 20% | L1 |
| S5-2 | 0.25 | 290 | 40 | 20% | L2 |
| S5-3 | 0.25 | 290 | 40 | 20% | L3 |
| S5-4 | 0.25 | 290 | 40 | 20% | L4 |
| S5-5 | 0.25 | 290 | 40 | 20% | L5 |
| S5-6 | 0.25 | 290 | 40 | 20% | L6 |

FIGS. 14A-14B show the experimental results of using probes S5-1 to S5-6 to collect the fluorescence from R6G.

From the FIGS. 14A-14B the L1 and L2 locations were similar but when the sample was close enough to the grating, then the collected signal was raised up. This is because there was a loss in the air-cladded segment between the sample and the grating experienced by the higher order modes. However this loss is acceptably low. So, if the higher-order modes can directly couple to the lower-order modes they would be more efficient than while propagating in the air cladded segment before coupling. In the L6 location there is no coupling from the higher-order to the lower order modes. Therefore, what could be collected at the spectrometer when the sample was on the L6 location was a pure evanescent mode that can propagate towards the detector. This also shows that the collection efficiency of the optical probe is high because with CFG it is possible to collect from the bulk of the sample as well as the surface just around the fiber side-wall. By this test, it can be concluded that the best location of the sample was on the grating's first half (L4) segment. If the sample is placed at location L5 then there is an imperfect coupling and the signal is not as high as at the location L4.

Consequently, the optimized CFG has 40 periods with the period size of 290 μm and the laser power should be set to 2 W.

Verification and Test Results

It is possible to visualize the coupling of higher-order to lower-order modes by comparing the far-field patterns of the fiber modes at the free end facet of the fibers with and without grating.

Figure 15A:
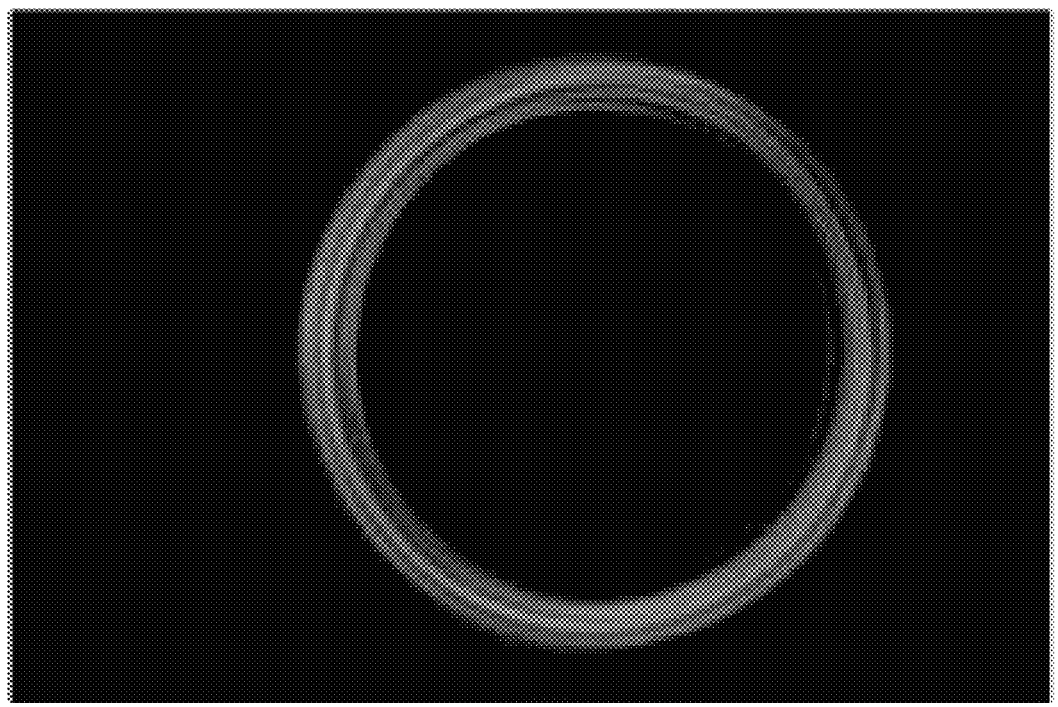
FIGS. 15A-15B are pictures of a far-field mode pattern taken from the free end facet of the fiber without and with corrugated grating, respectively, according to an embodiment of the present invention.
Figure 15B:

As shown in FIG. 15A, the far-field mode pattern of the fiber without grating consist of concentric symmetric rings close to the edge of the fiber surface. FIG. 15B shows the far-field mode pattern of the fiber with grating. The asymmetric pattern in Fig. FIG. 15B is appeared closer to the center of the fiber compare to the rings in Fig. FIG. 15A.

This can be an evidence of higher-order to lower-order coupling capability of the corrugated grating.

To examine the performance of the sensor, the corrugated fiber grating was used to collect the fluorescence released by the flurorophore: R6G at 555 nm. Then the same kind of fiber without any grating was used to collect the fluorescence released from the same sample. In this case what could be collected by the fiber was entirely from the intensity of the fluorescence coupled to the evanescent wave tail. Comparing these two signals proves the dramatic increase of the collectability of the corrugated fiber grating described herein.

Figure 16:
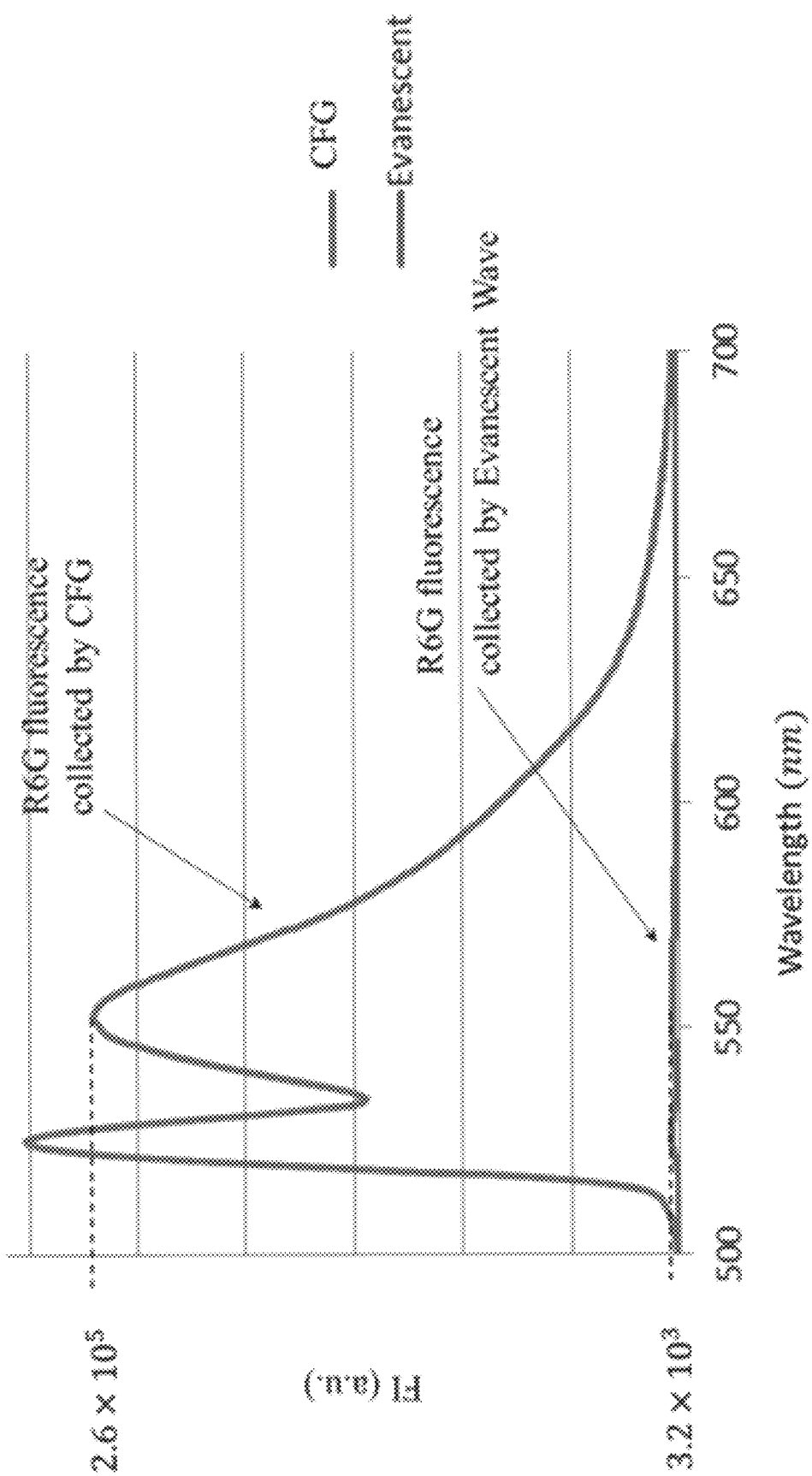
FIG. 16 is a graph illustrating R6G fluorescence collected by grating and by evanescent wave sensor, according to an embodiment of the present invention.

FIG. 16 shows the two signals achieved by the fiber probe and the bare fiber (pure Evanescent-wave).

Consequently, the experimental data shows that the corrugated fiber grating fabricated on highly multi-mode fiber, as previously described, intensely increases the collection efficiency of the optical fiber fluorescence sensor.

Multi-Channel Fluorescence Detection

There is described above a fiber optic structure for fluorescence detection using one channel. This structure can be used to detect some bio-chemical targets.

It is well known to use the end-face of a fiber to collect fluorescence; these types of sensors are bulk sensitive. On the other hand, side-wall of the fiber can be used for fluorescence collection based on evanescent-wave coupling. These types of structures are surface sensitive.

Although the single-channel (i.e., single-grating) sensor described above uses the side-wall of the fiber, it is bulk sensitive, i.e., it can detect fluorescence from the depth of liquid sample. Another point is that the length of the sensing area is limited to a few millimeters. Therefore several channels can be fabricated along the fiber to form a multi-channel fluorescence sensor. The resulting sensor is therefore not bulk-sensitive and has a sensing area with increased length.

The main issue in the multi-channel sensors is to minimize the cross-talk between channels. The basic idea of making several channels in one fiber with reasonably low cross-talk is to use the asymmetric nature of corrugated fiber grating. When a corrugated grating is used to couple higher order modes to the lower order core modes, the asymmetric modes are excited. The mode pattern of these modes on the fiber cross-section is asymmetric, as shown in FIG. 15B.

This pattern is highly affected by the grating's orientation (θ) and the distance between grating and cross-section (L) plane. These two parameters can be used to minimize the cross-talk between two channels.

Fabrication Set-Up

Figure 17:
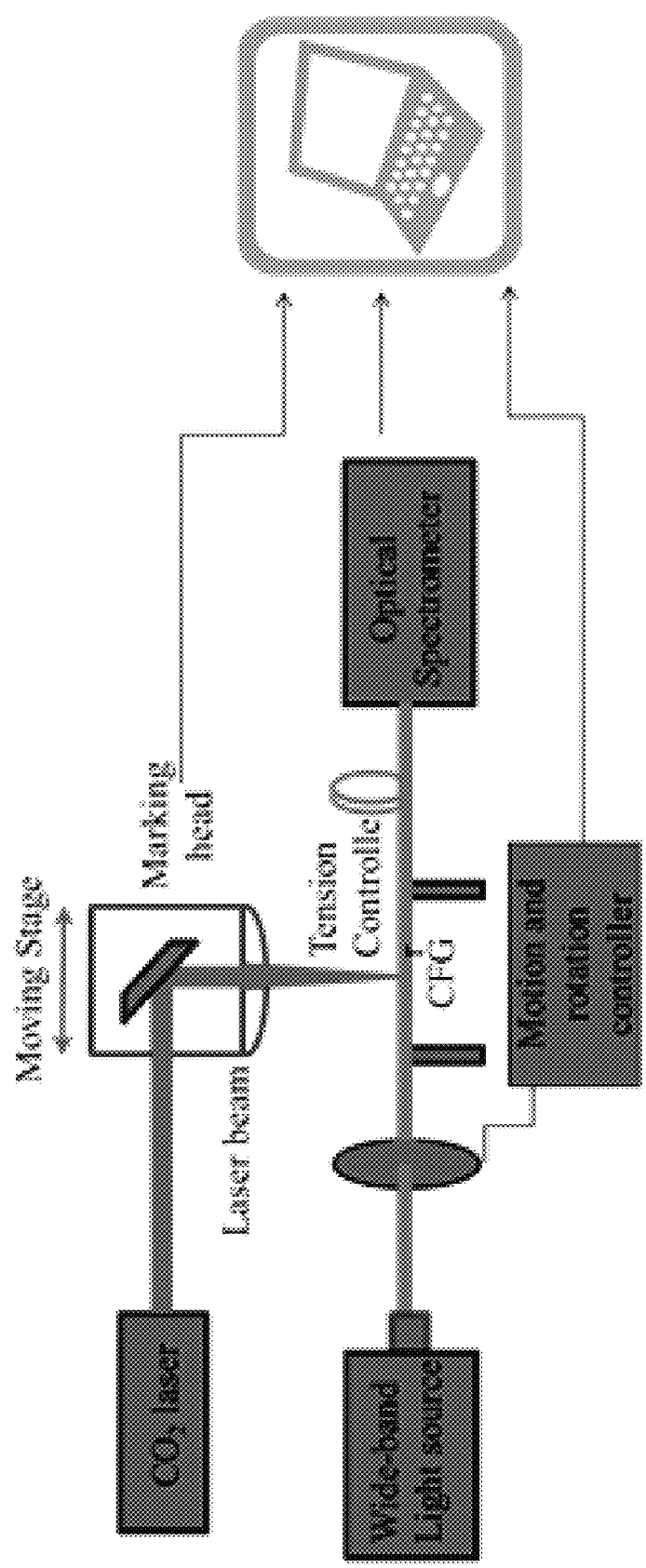
FIG. 17 is a diagram illustrating a multi-channel sensor configuration fabrication set-up, according to an embodiment of the present invention.

The fabrication setup is slightly changed from the one which is described above in reference with FIG. 5 to add the rotation and motion ability of the fiber around and along its axis, respectively. FIG. 17 shows the fabrication settings to make two channels on a single fiber.

Using this set-up, one can make two channels (or more) with the separation ranging from few millimeters to few centimeters. Moreover, it is possible to rotate the fiber and make two gratings on different sides of the fiber. In this case, in cylindrical coordinates, the fiber extends in a longitudinal axis and the gratings are provided at different azimuths (i.e., the angle around the fiber) on the fiber.

Figure 18A:
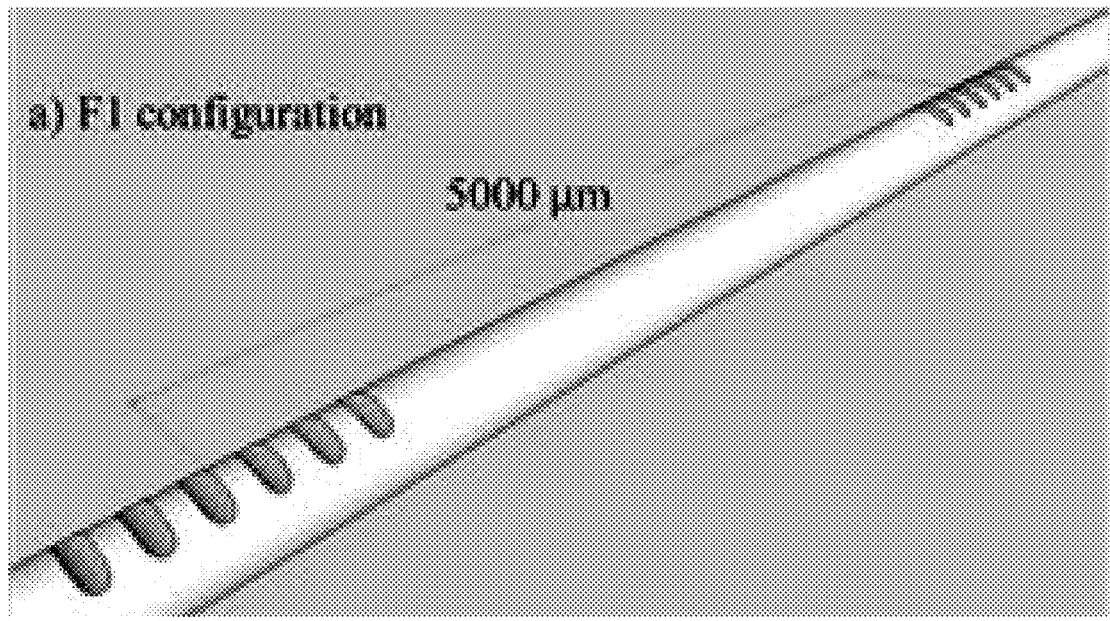
FIG. 18A is a perspective view illustrating parallel channels with θ=0 and L=5000 μm (F1 configuration), according to an embodiment of the present invention.
Figure 18B:
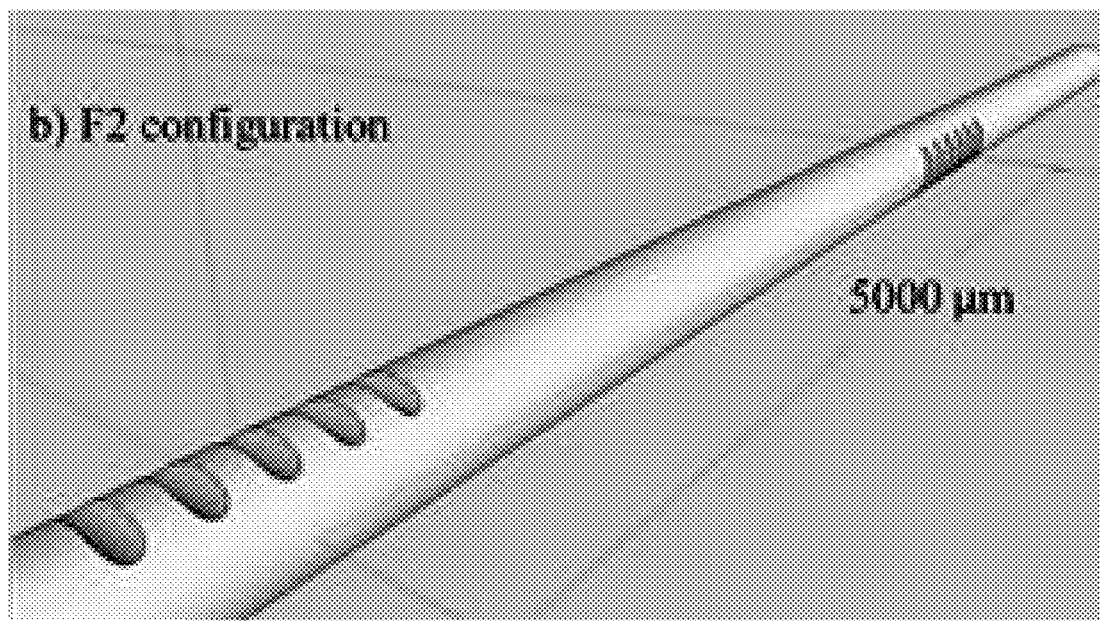
FIG. 18B is a perspective view illustrating perpendicular channels with θ=90° and L=5000 μm (F2 configuration), according to an embodiment of the present invention.

There are shown in FIGS. 18A-18B two different embodiments of fiber probes, each of them having two channels on the side-wall. In the first configuration (called F1) shown in FIG. 18A, two gratings are imprinted on the same side (i.e., same azimuth) of the fiber probe with the separation distance of L. However, in the second configuration (called F2) shown in FIG. 18B, after imprinting the first grating, the fiber is rotated by 90 degree and then the second grating is imprinted at an azimuth which differs of 90° from the first grating. In both F1 and F2 the distance (longitudinal spacing) between two gratings is kept fixed and equal to L=5 cm from the middle to middle of the gratings; however, this distance could vary in other embodiments.

Experiments and Test Results

Using configurations F1 and F2, there were designed several experiments to demonstrate the ability of controlling the cross-talk by controlling the relative angle of the two channels (θ), where θ is the difference in azimuths of two gratings, supposing that all valleys in a particular grating are all imprinted with the same azimuth. The measurement set-up is similar to the one used for single channel in FIG. 27. The only difference is the ability to move the fiber along its axis (i.e., longitudinally) to reach both channels for measurements.

To test the impact of the first channel (CH1) and the second channel (CH2) on each other, some experiments were designed. In these experiments, there was used a Rhodamine 6G fluorescent solution in two different roles. The first role was to use R6G as an excited droplet, which illuminates fluorescence while the second role was to use it as a test droplet. An excited droplet could be placed on CH1 or CH2.

Figure 19A:
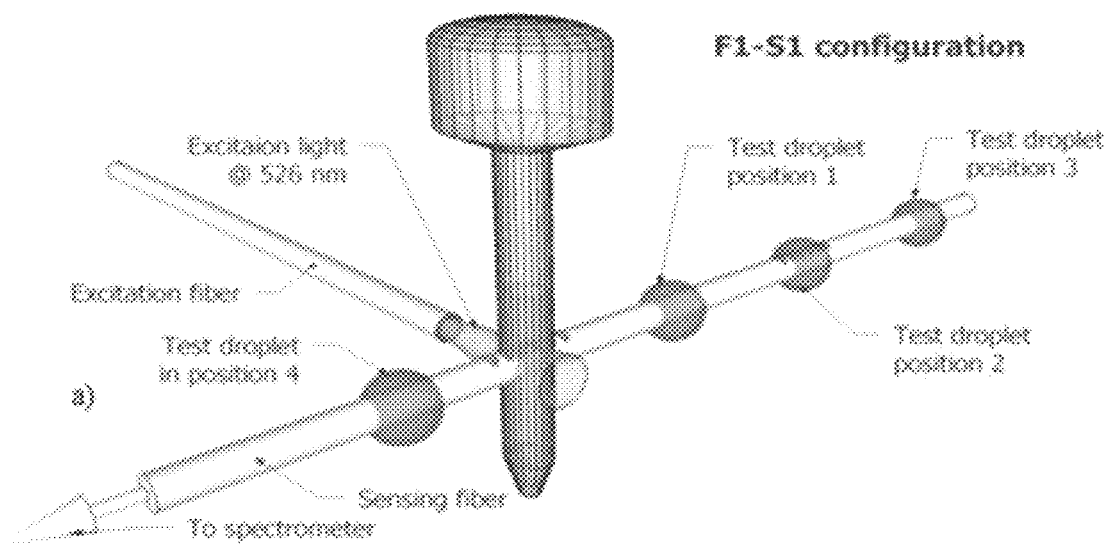
FIGS. 19A-19D are perspective views illustrating four experimental configurations for performing basic verifications, according to an embodiment of the present invention.
Figure 19B:
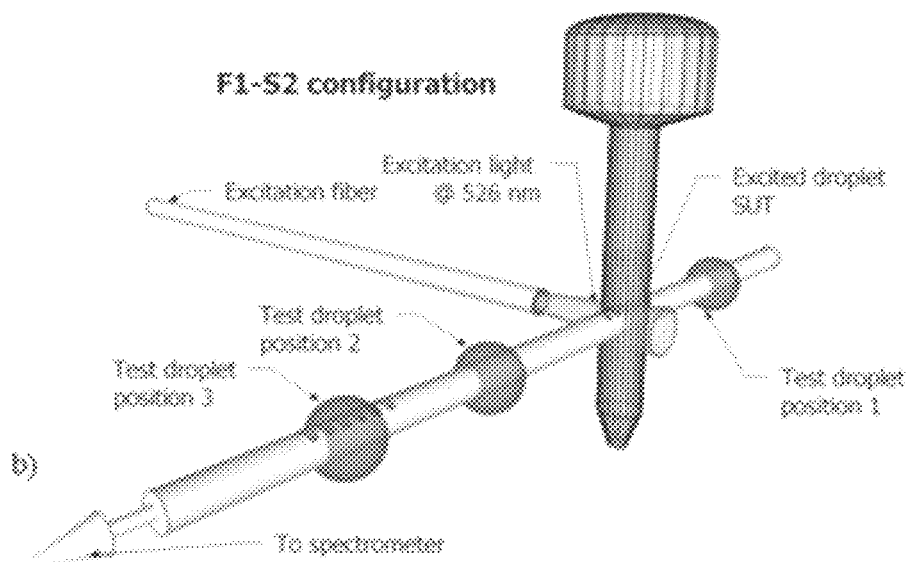
Figure 19C:
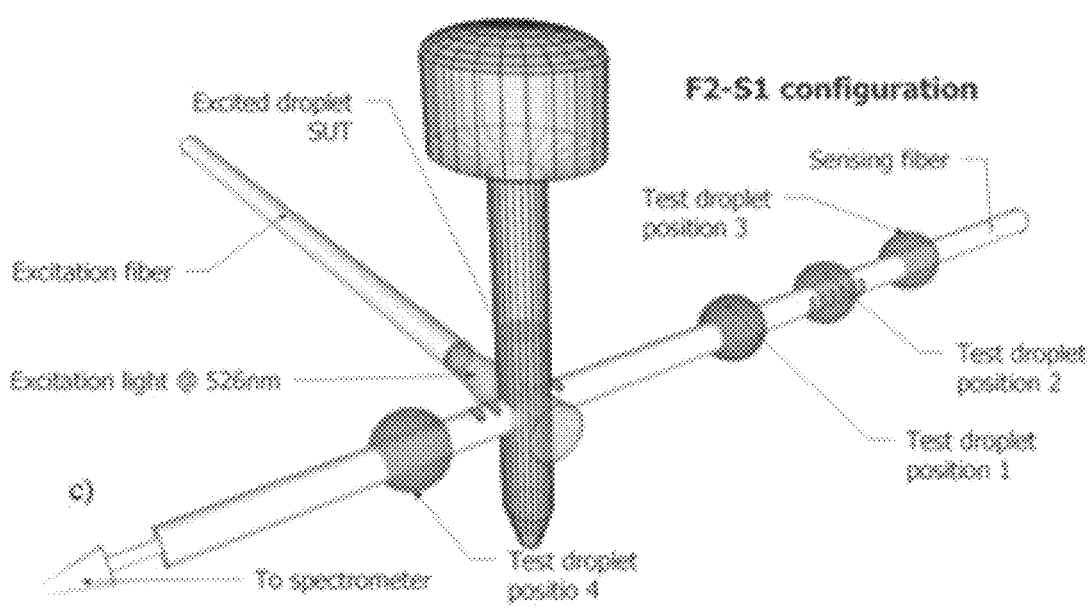
Figure 19D:
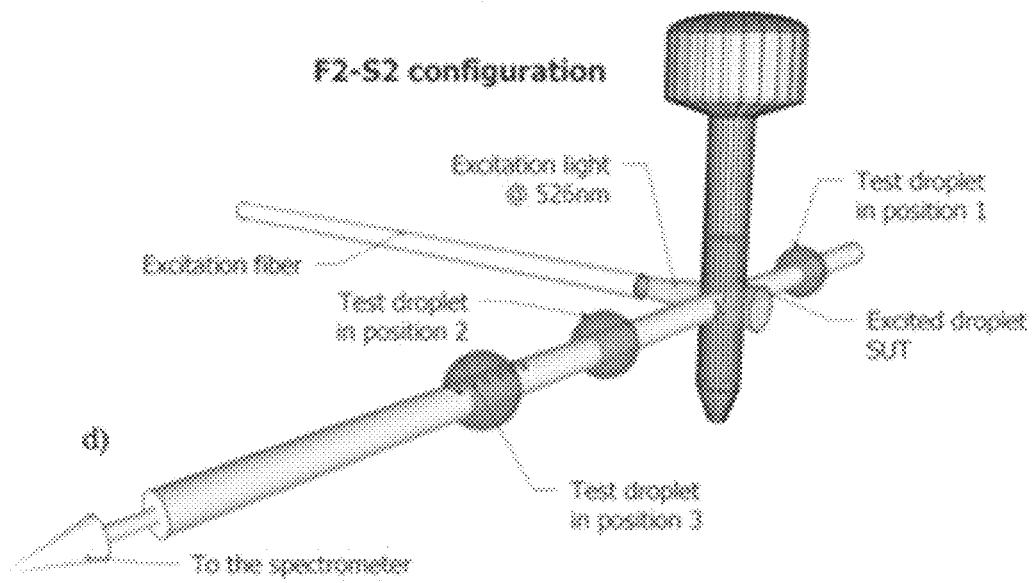

FIG. 19A: F1-S1 configuration: two parallel channels, excited droplet (SUT) on first channel (CH1), test droplet on second channel (CH2);

FIG. 19B: F1-S2 configuration: two parallel channels, excited droplet (SUT) on second channel (CH2), test droplet on first channel (CH1);

FIG. 19C: F2-S1 configuration: two perpendicular channels, excited droplet (SUT) on first channel (CH1), test droplet on second channel (CH2);

FIG. 19D: F2-S2 configuration: two perpendicular channels, excited droplet (SUT) on second channel (CH2), test droplet on first channel (CH1).

Test droplets can be placed anywhere along the fiber to check the fluorescence intensity released by excited droplet in presence of test droplets. Based on the location of the excited droplets, there are two steps. FIGS. 19A-19D show different configurations based on the excited and test droplets' locations. There are defined step 1 (S1) and step 2 (S2) when the excited droplets were on CH1 and CH2, respectively.

There were put test droplets on different parts of the fibers in order to analyze the fluorescence changes. Therefore, several combinations of F1, F2, S1, S2 were tested, with locations of test droplets numbered from 1 to 4 as shown in FIGS. 19A-19D.

The fluorescence captured by each configuration can be analyzed to draw some conclusions.

Figure 20A:
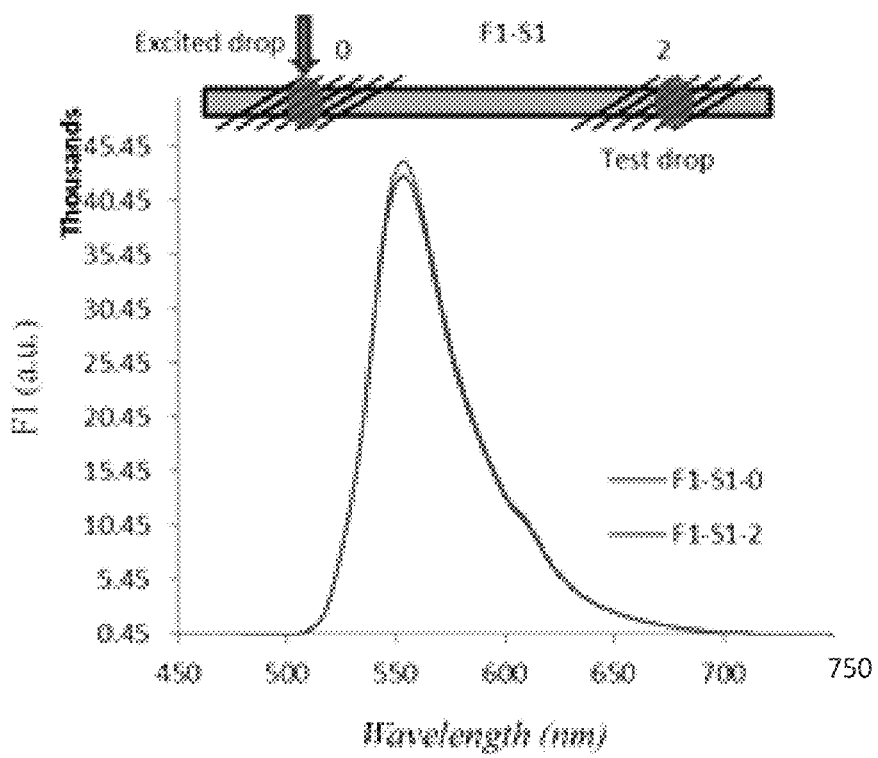
FIGS. 20A-20B are graphs illustrating the effect of the addition of a test droplet on CH2 when the excited droplet is on CH1 for fiber F1 and F2, according to an embodiment of the present invention.
Figure 20B:
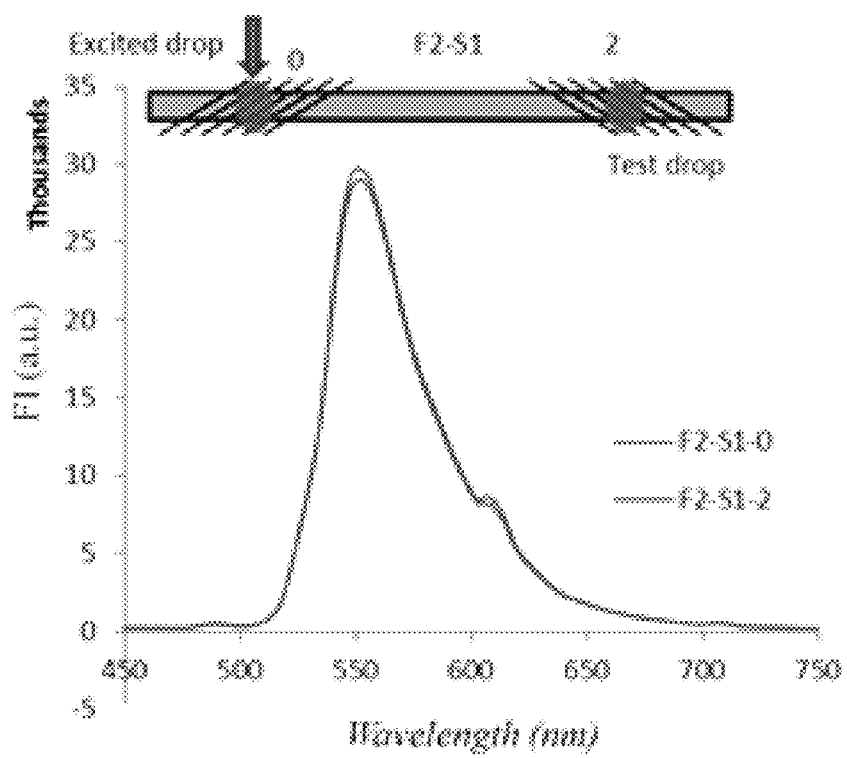

The signal captured by the F1-S1 configuration (using F1, excited droplet on CH1) shows that by adding a test droplet on CH2 the signal loss is 3% of the total intensity as illustrated in FIG. 20A. This loss for the same configuration on fiber probe F2 (F2-S1) is 2% as shown in FIG. 20B.

Figure 20C:
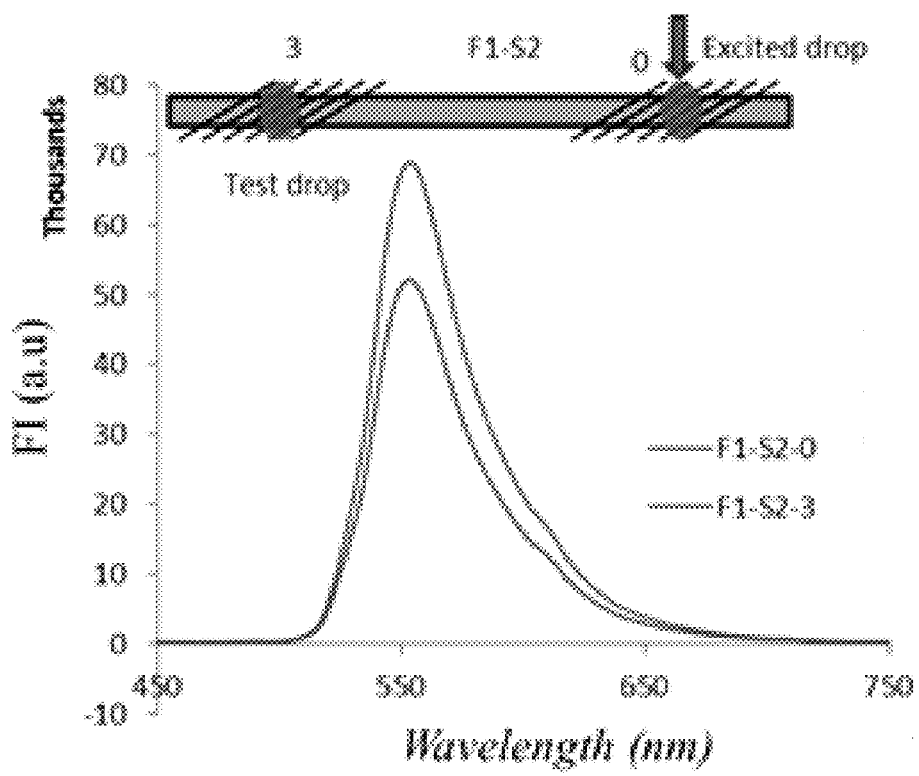
FIGS. 20C-20D are graphs illustrating the effect of the addition of a test droplet on CH1 when the excited droplet is on CH2 for fiber F1 and F2, according to an embodiment of the present invention.
Figure 20D:
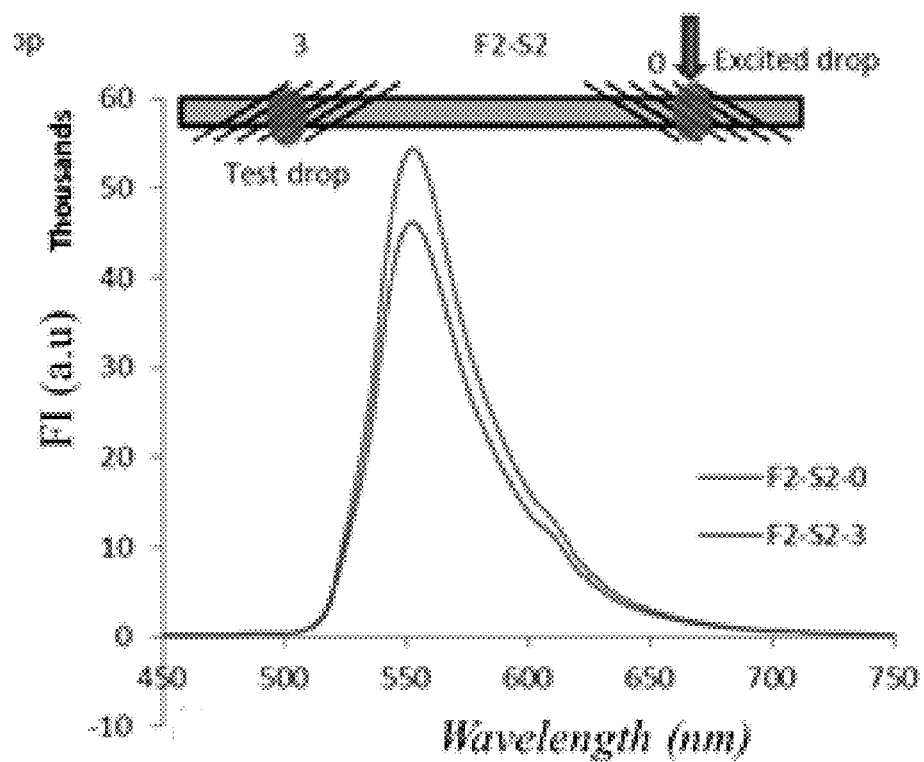

On the other hand, for the configuration F1-52 (using F2, excited droplet placed on the CH2) by adding test droplet on the CH1 the fluorescence intensity drops by 24% as shown in FIG. 20C. For the same configuration on fiber probe 2 (F2-S2), by adding the test droplet to the CH2, the fluorescence intensity drops by 15%, as shown in FIG. 20D.

Unlike cross-talk of CH2 on CH1 (2%-3%), the cross-talk of CH1 on CH2 depends on what kind of fiber probe configurations is used. This shows the impact of the grating's orientation (θ) on the cross-talk between two channels.

In order to minimize the cross-talks, two parameters, θ and L, have to be adjusted. This adjustment could be accomplished by an extensive experimental work in a different project that can be done in future. One of the possible ways to find the best combinations of location and orientation of two channels is to observe the modal pattern at different fiber cross-sections. The best place to imprint the second channel is where the intensity coming from the first channel is minimum. This way the impact of second channel on the first channel's signal can be minimized.

Application to Heavy Metal Ion Detection

Figure 31:
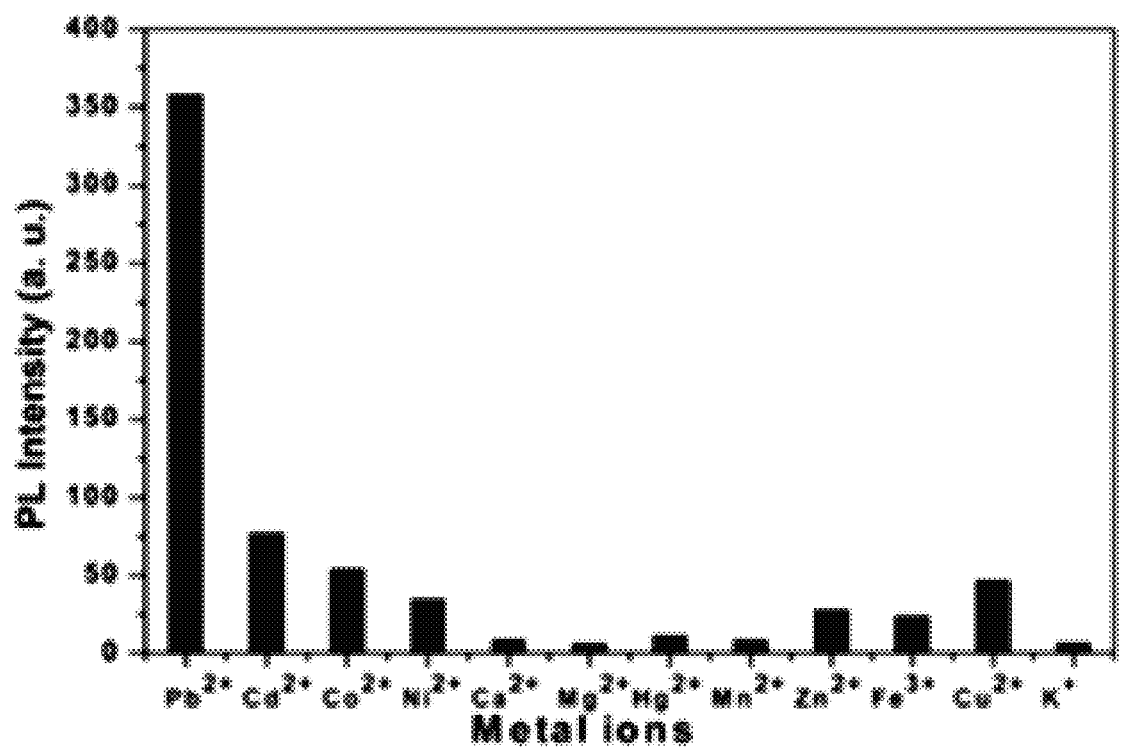
FIG. 31 is a graph illustrating relative fluorescence intensities of a 7a fluorophore solution towards different metal ions, according to an embodiment of the present invention.

In the field of heavy metal detection, such as $Cu^{2+}$ and $Pb^{2+}$, fluorescence spectroscopy can be used because of its high sensitivity, selectivity, simple application, and low cost. The detection of various heavy metal ions can be contemplated, e.g., $Cu^{2+}$, $Pb^{2+}$, $Co^{2+}$, $Ni^{2+}$, $Zn^{2+}$, $Cd^{2+}$, $Hg^{2+}$, $Ca^{2+}$, $Mg^{2+}$, $Mn^{2+}$, $Fe^{3+}$, $K^+$, or combinations thereof, as shown in FIG. 31 which illustrates the relative fluorescence intensities of a 7a fluorophore solution towards different metal ions. Preferably, the heavy metal ion may be $Cu^{2+}$, $Pb^{2+}$, or combinations thereof. Some small molecules have been demonstrated to be useful for the fluorescence turn-on detection of lead ions (i.e., $Pb^{2+}$) in the mixture of water and organic solvents or in a buffer solution. In particular, Chang et al. reported a water-soluble fluorescent probe (leadfluor-1) with a detection limit of 23 μM for lead ion. Conjugated polymers have been explored particularly for amplified fluorescence detection of aromatic nitro-containing compounds and other hazard chemicals.

Fluorometry methods can be categorized into two main groups. Fluorescence quenching methods, in which the background fluorescence will be quenched upon presence of a specific chemical target, are the more popular group. In other words, the target chemical is absorbed by a selective chemical receptor. This reaction causes the quenching of the background fluorescence that previously was released. On the other hand, the second category of fluorescence detection is turn-on fluorescence method. In this type of detection, there is no background fluorescence. The fluorescence will be raised upon the presence of the target chemical. This category of the sensors is known for their sensitivity due to the absence of background intensity. Optical fibers are used even as just a fluorescence collector of an external fluorescence source, or as a lab-on-a-fiber platform to incubate the acceptor and fluorophore on the fiber for better collectivity, selectivity and easy-to-use purposes. The evanescent tail of the fluorescent light is used to couple the light from the sidewall into the guided modes in the latter kind of the fluorescence sensor. The evanescent tail of the light can naturally couple a few percent of the total intensity to the fiber guided modes. Therefore, collecting the detectable intensity using these sensors needs enhancement considerations, such as lengthening the sensing area to which the sample under the tests (SUT) is exposed for better collectability, or using a tapered fiber to convert the higher order modes to the lower order one for lossless propagation. There were obtained sensitive and selective chemical polymers and small molecules for detection of $Cu^{2+}$ and $Pb^{2+}$ in water with the Chemistry group from Carleton University's contribution. Then these chemical probes can be successfully applied on the presently described optical fiber platform to form a reliable and efficient heavy metal detection tool targeting $Cu^{2+}$ and $Pb^{2+}$. This work easily can be extended to other chemical targets as long as the selective chemical probe is available.

The fluorescent molecular sensors use compounds that undergo a change in fluorescent properties like intensity and color upon binding a target molecule. Once a molecule is excited by absorption of a photon, it can return to the ground state with emission of light, but there are many other pathways for de-excitation, such as internal conversion, intramolecular charge transfer, conformational change, electron transfer, photon transfer, energy transfer, excimer formation, exciplex formation, photochemical transformation, phosphorescence and delayed fluorescence.

Figure 21:
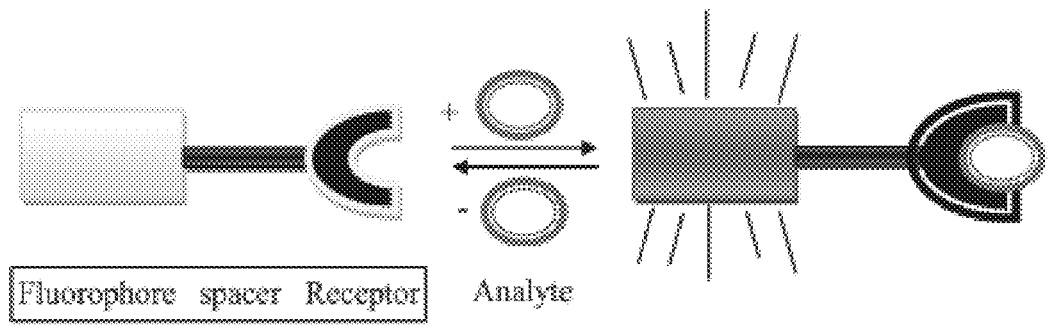
FIG. 21 is a diagram illustrating a fluorescence turn-on sensor, according to an embodiment of the present invention.

A fluorescent molecular sensor has three parts (FIG. 21) for molecular recognition and signal transduction, Receptor, Spacer and Fluorophore.

A receptor is able to selectively bind with a specific analyte. The spacer has an ability to change the geometry and the electronic interaction between the receptor and fluorophore. The fluorophore is the signaling species, i.e. it acts as a signal transducer that converts the information (presence of an analyte) into an optical signal expressed as the changes in the photophysical characteristics of the fluorophore.

Fluorescence quenching is the decrease in the fluorescence intensity after the interaction of an analyte with its receptor. A variety of molecular interactions, like excited state reactions, molecular rearrangements, energy transfer, ground-state complex formation and collision, can quench the fluorescence. In general, the mechanism of fluorescence quenching can be realized as either dynamic or static processes, but in some cases by both of them. The dynamic quenching mechanism results from diffusive encounters between the fluorophore and the quencher during the lifetime of the excited state. A wide variety of molecules can act as collisional quenchers, for instance, oxygen, halogens, amines and electron deficient molecules. In the static process, fluorescence quenching occurs as a result of the formation of a non-fluorescent ground state complex between the fluorophore and the quencher. This kind of quenching causes a sharp change in the absorption spectra of the fluorophore. In a liquid solution, the fluorescence quenching depends on the solvent viscosity, polarity, and pH of the medium. For donor acceptor systems, usually in the non-polar solvents the mechanism of quenching is the formation of an excited charge-transfer complex while in the polar solvents, such as water, it is the simple quenching. Quenching by heavy atoms may be as a result of an intersystem crossing to an excited triplet state, promoted by spin-orbit coupling of the excited (singlet) fluorophore and halogens. Quenching by metal ions involves the donation of an electron from the fluorophore to the metal ion.

Figure 22:
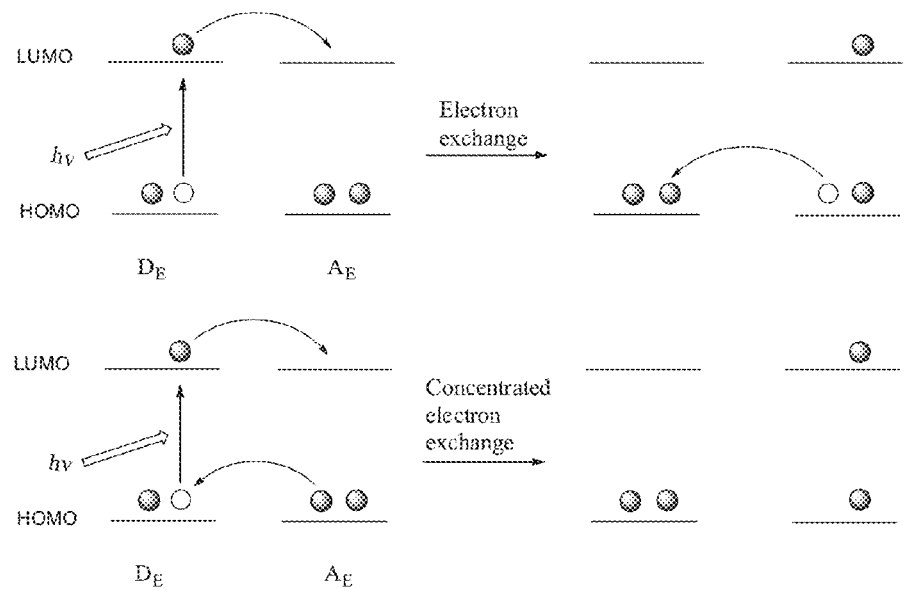
FIG. 22 is a schematic diagram illustrating electron exchange for fluorescence quenching, according to an embodiment of the present invention.

FIG. 22 shows the electron exchange or Dexter interaction. DE, AE, HOMO and LUMO represent the donor, acceptor, highest occupied molecular orbital and lowest unoccupied molecular orbital. The excited donor has an electron in LUMO orbital. This electron transfers to the LUMO of the acceptor, then the acceptor transfers an electron from its HOMO to the donor's HOMO and the acceptor is left in the excited state. This is happening when the distance between the donor and acceptor is large. In contrast, when the distance is short in a concentrated medium, Dexter transfer can occur. In both cases the acceptor stays in the excited state.

Fluorescence turn-on is the process in which there is an increase in the fluorescence intensity after the interaction of an analyte with its receptor. There are different ways to design a fluorescence sensor including intra-molecular charge transfer (ICT), metal-ligand charge transfer (MLCT), twisted intramolecular charge transfer (TICT) and photoinduced electron transfer (PET). Among them, the main focus here is on PET based fluorescence turn-off-on system. In PET turn-off or -on processes when an analyte binds with the receptor part, the electron transfer from the receptor to the fluorophore would either hinder (turn-on) or start (turn-off) the fluorescence.

Figure 23:
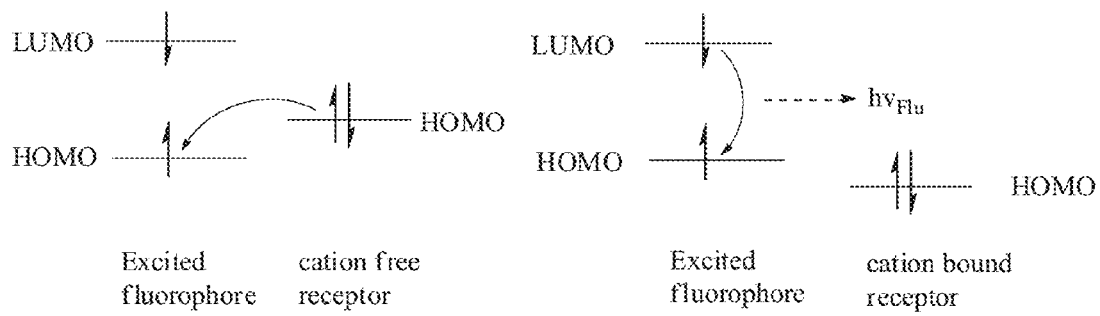
FIG. 23 is a diagram illustrating a frontier orbital energy representation of PET (turn on) in a "fluor-spacer-receptor" signaling system when cation (positive ion) is free (left) and when cation is bound (right), according to an embodiment of the present invention.

FIG. 23 displays the frontier orbital energy system for PET based fluorescence sensor systems. Most fluorescent PET molecular sensors consist of a fluorophore linked to an amine moiety via a methylene spacer. Photoinduced electron transfer which takes place from the amino groups to aromatic hydrocarbon causes fluorescence quenching of the latter. When the amino group strongly interacts with a cation, electron transfer is hindered and a very large enhancement of the fluorescence is observed. The cation free and cation binding phenomenon is called turn off-on fluorescence. The mechanism in terms of the molecular orbital (FIG. 23), shows that upon excitation of the fluorophore, an electron of the HOMO is promoted to the LUMO. As a result PET from the HOMO of the donor (cation-free receptor) transfers to that of the fluorophore, causing fluorescence quenching of the latter. When cations bind, the redox potential of the donor is raised so that the relevant HOMO becomes lower in energy than that of the fluorophore; as a result, PET is no longer possible and fluorescence quenching is suppressed.

$Pb^{2+}$ Detection

Lead ion as a heavy metal is highly toxic and can be absorbed by plants and animals and entered into the human body. On the chemical side, the chemical probes should be used for selective sensing. Using a turn-on polymer solution which has high selectivity to the $Pb^{2+}$, low concentrations of lead ions (selective sensing) could be detected in water by the developed CFG based fiber-optic fluorescence sensor.

Chemical Probe Characterization

The chemical probe is a chemical compound or a polymer that is used to functionalize the fiber-optic sensor and is placed on its surface. This chemical probe reacts to the presence of $Pb^{2+}$ in the solution. The chemical procedure to make materials which can be used on the fiber-optic sensor has been discussed with details in Saha et al. (S. K. Saha, K. R. Ghosh, W. Hao, Z. Y. Wang, J. Ma, Y. Chiniforooshan, and W. J. Bock, "Highly sensitive and selective fluorescence turn-on detection of lead ion in water using fluorene-based compound and polymer," Journal of Materials Chemistry A 2, 5024-5033, 2014) in its experimental section. Consequently after several sequences the most sensitive chemical compound for $Pb^{2+}$ detection, which is named compound 7a, was obtained. In addition, some polymer solutions named P1, P2, P3 have been made by a chemical process as mentioned above for higher sensitivity. The sensitivity and selectivity of these chemical probes were analysed. Below is the result of chemical characterization of the materials to be used on the fiber-optic sensor.

Detection of $Pb^{2+}$ in Water Using Compound 7a

Figure 24:
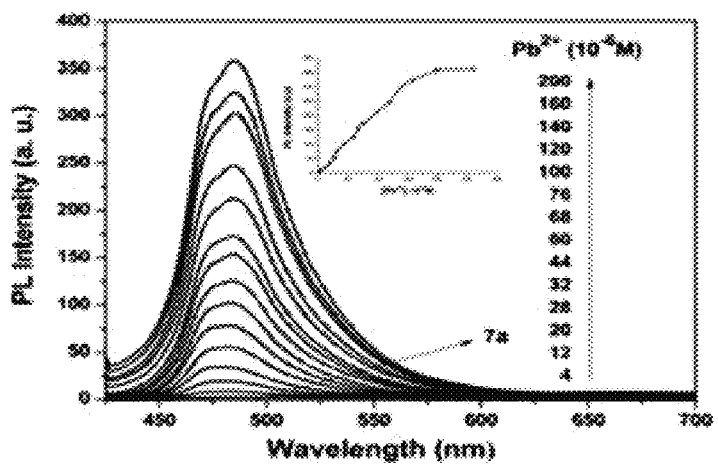
FIG. 24 is a graph illustrating changes of fluorescence spectra of 7a in water ($2.8 \times 10^{-4}$ M) upon addition of $Pb^{2+}$ (0 to $200 \times 10^{-6}$ M) (excitation at 400 nm), according to an embodiment of the present invention.

The high sensitivity of the compound 7a towards $Pb^{2+}$ was revealed by a fluorescence spectroscopic titration experiment. FIG. 24 displays the change in fluorescence of 7a with different concentration of $Pb^{2+}$.

Compound 7a is virtually not fluorescent. Upon addition of the $Pb^{2+}$ solution in a concentration as low as 4 µM, its fluorescence turns on noticeably. The emission intensity at 489 nm increased sharply, nearly 152-fold after an increase in the $Pb^{2+}$ concentration up to 200 µM. For Chang's probe 1, after addition of 75 µM of $Pb^{2+}$ solution to Leadfluor-1, its fluorescence intensity increased 18-fold; the same increase of intensity was achieved by 7a with the addition of only 24 µM of $Pb^{2+}$ solution. The addition of 15 ppb of $Pb^{2+}$, which is the maximum EPA limit for the allowable level of lead in drinking water, to a solution of 7a (1.4×10-4 M) triggers a 23% increase in fluorescence intensity, which is stronger than the reported probe (15% increase). Upon addition of $Pb^{2+}$ the absorption wavelength (402 nm) of compound 7a in solution (5×10-5 M) does not change but the absorption intensity gradually decreases. These results indicate that fluorene is a suitable fluorophore, which makes compound 7a a highly sensitive molecular probe for $Pb^{2+}$ detection in aqueous media.

The stoichiometry for $Pb^{2+}$-7a binding was determined using the Job's plot method. For the measurement of the Job's plot, aqueous solutions of $Pb^{2+}$ and 7a in various molar ratios (2:8, 3:7, 4:6, 5:5, 6:4, 7:3, 8:2, 9:1, 10:0) were prepared. The relationship between relative emission intensity versus various mole fraction shows that compound 7a-$Pb^{2+}$ complex is formed in a 1:1 molar ratio.

The fluorescence turn-on mechanism can be explained as follows: the $Pb^{2+}$-pseudo-macrocyclic complex facilitates electron transfer from the nitrogen to lead ions. Thus, the redox potential of the electron donor in 7a-$Pb^{2+}$ complex is raised so that the relevant HOMO level becomes lower than that of the free fluorophore. As a result, photoinduced electron transfer (PET) is no longer possible in the system and the fluorescence of the fluorophore turns on.

Figure 25:
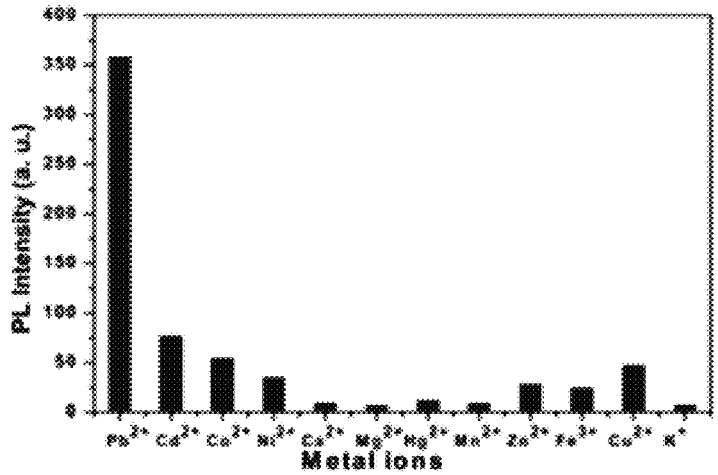
FIG. 25 is a graph illustrating the relative fluorescence intensity of 7a solution ($2.8 \times 10^{-4}$ M in water) towards different metal ions, according to an embodiment of the present invention.

The selectivity of compound 7a in the presence of different alkali, alkaline earth, transition and heavy metal ions ($K^+$, $Ca^{2+}$, $Mg^{2+}$, $Mn^{2+}$, $Fe^{3+}$, $Co^{2+}$, $Ni^{2+}$, $Cu^{2+}$, $Zn^{2+}$, $Cd^{2+}$, $Hg^{2+}$) was investigated using a spectroscopic method. After the addition of 200 µM of individual metal ions to a solution of 7a (2.8×10-4 M in water), the emission intensity at 489 nm from each spectrum was taken and compared against each metal ion (FIG. 25). A relatively strong emission of compound 7a towards $Pb^{2+}$ over these 11 metal ions clearly indicates its high selectivity for the detection of $Pb^{2+}$ in an aqueous medium. Some metal ions such as $Ca^{2+}$, $Cd^{2+}$, $Hg^{2+}$ and $Mn^{2+}$ are known as interfere with the detection of $Pb^{2+}$. In the instant case, $Cd^{2+}$, $Co^{2+}$, $Cu^{2+}$, show little interference. The selectivity of compound 7a towards $Pb^{2+}$ over these 11 metals demonstrates that dicarboxylate pseudo crown receptor can selectively bind with $Pb^{2+}$ (FIG. 25).

Detection of Pb2+ in an Aqueous Medium Using a Polymer

Figure 26:
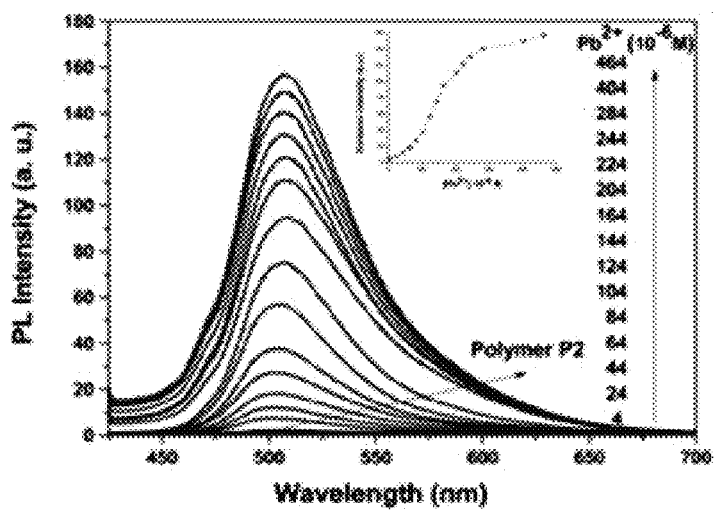
FIG. 26 is a graph illustrating changes of fluorescence spectra of polymer P2 ($2.8 \times 10^{-4}$ M) in pure water-THF (1:1) upon addition of $Pb^{2+}$ (0 to $464 \times 10^{-6}$ M) (excited at 400 nm), according to an embodiment of the present invention.

Electrons in conjugated polymers are highly mobile and can migrate throughout the polymer chain. This migration increases the frequency of interaction with the bound quencher, and as a result the sensitivity becomes higher. The sensitivity of polymer P2 (2.8×10-4 M) towards $Pb^{2+}$ was determined by a fluorescence spectroscopic titration experiment (FIG. 26) upon addition of 4 µM of $Pb^{2+}$, the fluorescence of P2 turned on noticeably. The emission intensity of polymer P2 at 509 nm increased sharply in a water-THF (1:1 v/v) solution by nearly 134 fold with an increase of the concentration of $Pb^{2+}$ from 0 to 464×10-6 M. Polymer P2 shows the same sensitivity towards $Pb^{2+}$ as the compound 7a. The addition of 15 ppb of Pb2+ (the max EPA limit) to a solution of polymer P2 (2.8×10-4 M) triggered an increase in fluorescence intensity of 26%.

As an analog to P2, polymer P3 is in the acidic form, and a 20 nm bathochromic shift in the maximum emission wavelength from 509 nm to 529 nm was observed. Upon addition of $Pb^{2+}$ up to 584×10-6 M, the fluorescence intensity of P3 (2.8×10-4 M in DMF) at 529 nm increased only 26 fold. Inefficient binding to $Pb^{2+}$ by P3 is mainly due to the nature of the carboxylic acid and by converting the acid to the salt, the sensitivity of P3 towards the lead ion should increase. Thus, after addition of LiOH to the solution of P3, the fluorescence intensity at 509 nm increased 164 fold in presence of $Pb^{2+}$. Accordingly, sensory compound 7a and polymer P2 or P3 in the salt state are active to detect $Pb^{2+}$ in water. Both compound 7a and polymer P2 give the same level of fluorescent signal towards 15 ppb of $Pb^{2+}$.

Fiber Optic Probe

The optical fiber fluorescence sensor based on corrugated fiber grating (CFG) was used to detect lead ions in water. The optical platform has been described above in reference with FIG. 1. The fiber structure consisted of a highly multi-mode optical fiber with CFG fabricated along the fiber on its un-cladded side-wall. The common application of the long period fiber gratings (LPFG) imprinted on single-mode fibers is to couple the core mode to the cladding modes at a certain wavelength. This causes a resonance in transmission spectrum for that specific wavelength. Unlike that common role in case of the single-mode fibers, there is use a corrugated fiber grating imprinted on highly multi-mode fiber to couple the higher order modes to the lower order core modes within a certain range of wavelengths. Higher order modes are excited by the fluorophores covering the fiber side-wall. Because of the wideband nature of the fluorescence spectrum, the coupling over the wide range of wavelengths would be beneficial for fluorescence detection applications.

The sample under the test (SUT) was a few microliters of water that may contain the chemical target ions and had been already mixed with the chemical probe. The chemical probe was a sensitive fluorescence turn-on polymer which was selective to the target ions. The target ions in this case were lead ions, and turn-on fluorescence was used as a chemical probe. The sample under test is thus considered as fluorescible (it can fluoresce).

If SUT is contaminated by the lead ions, the fluorescence would be released in SUT. The refractive index of SUT was close to the refractive index of water (1.33) which is lower than the core refractive index (1.46). The core modes of a fiber have effective indices ($n_{eff}$) between core ($n_{co}$) and cladding ($n_{polymer}$) refractive indices $n_{polymer}<n_{eff}<n_{co}$. On the other hand, all fluorescent light propagating in SUT has an effective index less than the water refractive index. Therefore the fluorescent light cannot excite the core modes of the fiber and they would exist as radiating modes. Excluding the small portion of evanescent coupling, this fluorescent intensity has huge loss and would radiate out of the fiber within a short distance unless radiating fluorescent intensity is coupled to the core modes. The role of the CFG in this sensor is to perform this coupling between the radiating and the core modes as described in section 4.5. By optimizing the parameters of the CFG for a certain fluorescent wavelength the fluorescence was coupled to the core of the fiber and let the fluorescent light propagate inside the core toward the detection system. It has been shown that the fluorescence released in a certain radial distance from the side-wall can be optimally coupled to the core of the fiber. This distance also can be set by controlling the CFG parameters. By doing so, one can focus on the events happening in certain layer around the fiber. Another parameter that needed to be considered was the length of the SUT along the fiber. Since a very short SUT leads to the low fluorescent intensity and a very long SUT causes the high loss for the released fluorescence, there was an optimized length in which the fluorescence collection efficiency could be maximized.

Fabrication

The corrugated fiber grating was fabricated using a CO2 laser beam and was optimized by the choice of grating parameters (e.g. period, length, depth) for a specific fluorescence wavelength. As explained in previous chapter, the optimized CFG has 40 periods with the separation distance of 290 μm. The laser power has to be set to about 2 W for the best results.

Measurements and Conclusion

Figure 27:
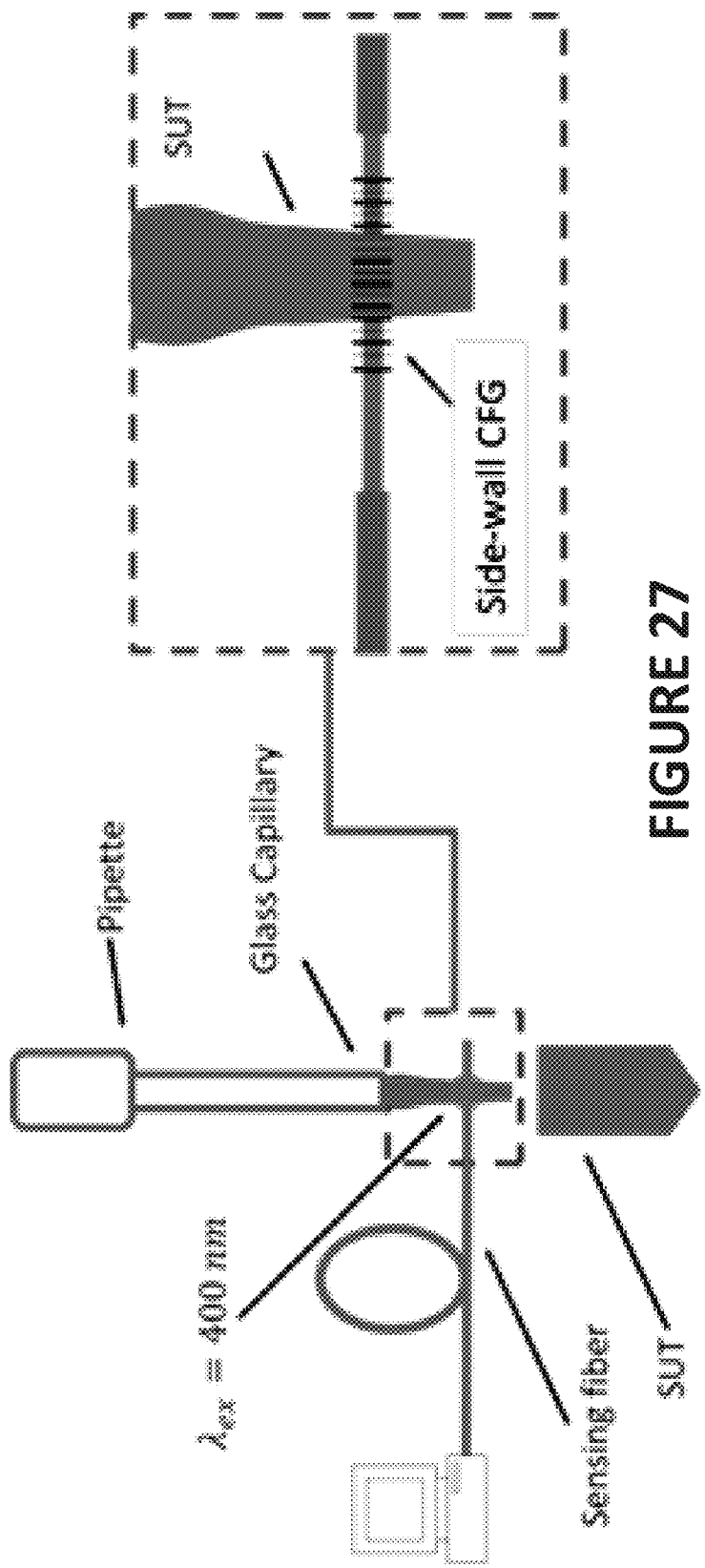
FIG. 27 is a diagram illustrating an instrumentation set-up of the optical fiber fluorescent sensor using fluorescence collection from the side-wall of a multi-mode fiber, according to an embodiment of the present invention.

The measurement setup is shown in FIG. 27. The SUT could be sucked up from the sample container by a pipet which had been drilled (by CO2 laser beam) to pass a large-core multi-mode fiber through it. The sample was excited by a collimated LED light at the excitation wavelength and perpendicular to the fiber axis. To test the sensitivity and limit of detection for this sensor some water solutions with different concentrations of lead ions had been prepared.

Figure 28A:
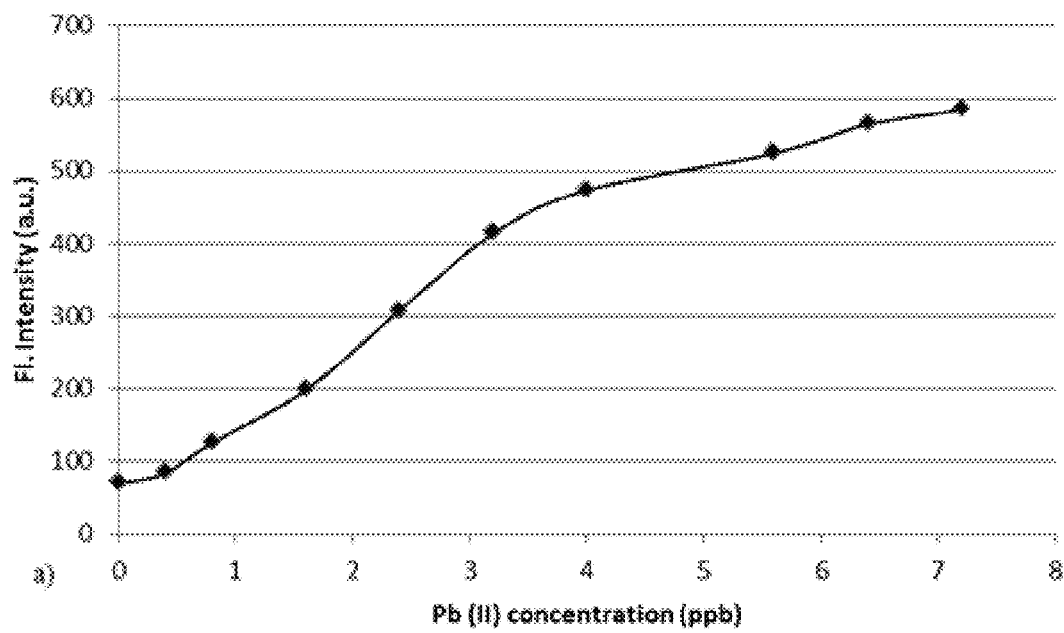
FIGS. 28A-28B are graphs illustrating lead ion concentrations in water detected by fiber optic fluorescence sensor that is enhanced by corrugated fiber grating, and a regression line for detection limit calculation, according to an embodiment of the present invention.
Figure 28B:
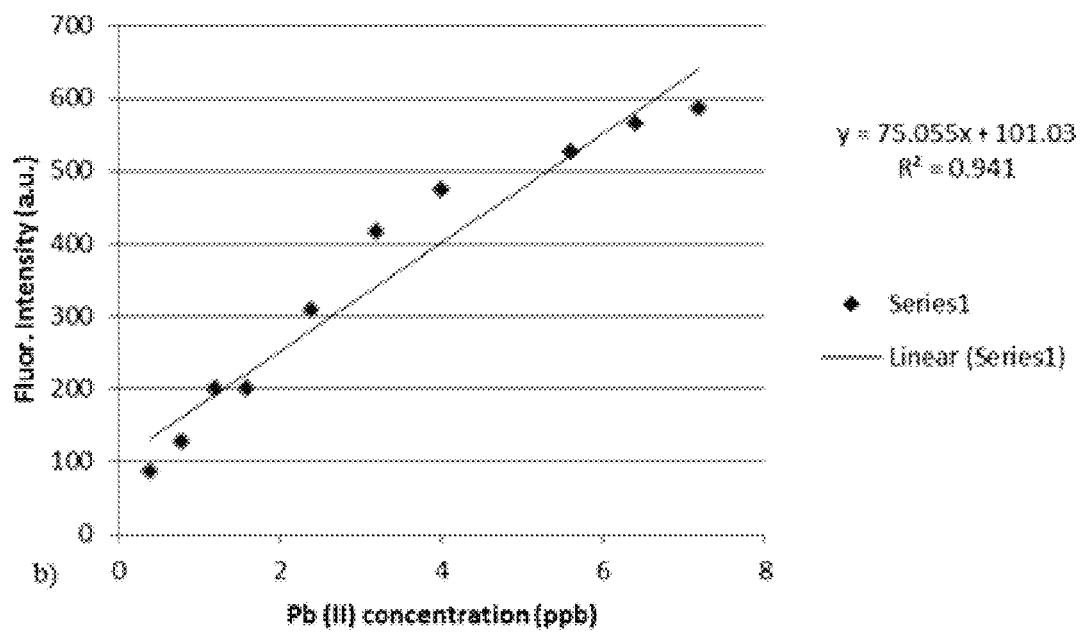

In FIGS. 28A-28B, the experimental peak value of the fluorescence captured by the sensor for different lead concentrations in water is shown. There were two sources of errors in this measurement. First was the error on determination of the measured lead concentration. This error was calculated to be 0.1 μg/L or 0.1 ppb.

The second source of error was the fluorescence intensity (FI) measurement error of the set-up shown in FIG. 27.

The fluorescence intensity measurement error was 7% of the total fluorescence change. Consequently, FIG. 28A shows that the minimum concentration of the lead ions that can be detected by this sensor using the measurement setup shown in FIG. 27 is about 1 μg/L or 1 ppb.

However there is a standard procedure to calculate the detection limit (DL) or limit of detection (LOD) of a system using the set of concentrations that could be detected by that system. By definition the detection limit (DL) can be expressed as 3 times of standard deviation of blank/slope of the calibration line. The DL is calculated from the regression line; assuming sB (standard deviation of the blank or background) is equal to sy/x (standard deviation of regression). By this approximation it is assumed that errors are normally distributed for each point and the variances of each point are equal and can be estimated by sy/x. Therefore the detection limit of $Pb^{2+}$ by the CFG-based fiber-optic fluorescence sensor is $1.94\times10^{-3}$ mg/L or 1.94 ppb.

Since in this sensor a small length of the side-wall (less than two centimeters) was used, there is a possibility of using also another channel along the fiber to detect in parallel different chemical material with its specific chemical probe.

In conclusion, an optimized corrugated fiber grating imprinted on the side-wall of a large-core multi-mode fiber was used to collect fluorescence from not only the surface but also from the bulk of the sample. Therefore, the sensor could be used as a multi-target device. The Environmental Protection Agency (EPA) has strictly regulated the concentration of lead ions in drinking water so as not to exceed 15 μg/L (or 15 ppb). The experimental results show that the detection limit of the concentration of lead ions for this sensor was much lower than the limit for lead contamination of drinking water as introduced by EPA regulation.

$Cu^{2+}$ Detection

Another heavy metal which can be detected using the fiber-optic fluorescence sensor is copper ions or $Cu^{2+}$ in water solution. In an experimental set-up, the chemical probe that was selective to copper ions was a fluorescence turn-off-on polymer. The polymer solution was prepared by dissolving a 2.9 mg fluorophore polymer in 1 ml of CHCL3 and further diluted in 10 ml of DMF solvent. Then 1 mL of this solution was diluted again in 10 mL of DMF. After filtering, the P1 solution was ready with the concentration of $3\times10^{-4}$ mol/L to generate the fluorescence. The Zwitterionic chromophore (M1) was synthesized and found to show high selectivity and sensitivity to $Cu^{+2}$ making the M1 an ideal receptor for recognition of $Cu^{+2}$. Moreover, M1 diluted in the DMF is a fluorescence turn-off of P1. Therefore, by adding M1 to P1 solution following the proper relative amount of solutions, the P1-M1 pair was made with a turned-off fluorescence radiation. The P1-M1 solution was used to detect the trace of copper in water. Adding a small amount of contaminated water to this P1-M1 solution could show the presence of copper ions. If copper ions are absorbed by M1 then the P1-M1 pair will be broken. Therefore, if the previously turned-off fluorescence starts to rise again, this would be the sign of presence of copper in water. In the next section, there are shown the experimental results of this sensor in application for detection of copper ions in water. The fiber optic platform as discussed in the previously was used to detect the copper ions. The measurement setup for this experiment was the same as the one was used for lead detection (FIG. 27). A micrometer capillary was placed in a sensing area with no contact to the fiber sidewall. This capillary was used to expose the SUT to the sidewall of the fiber and, more importantly, to stabilize the signal originated from the SUT. Using a suction mechanism, the solutions were put in contact with the sensing area of the fiber for fluorescing or cleaning purposes.

Experimental Results and Discussion

Figure 29:
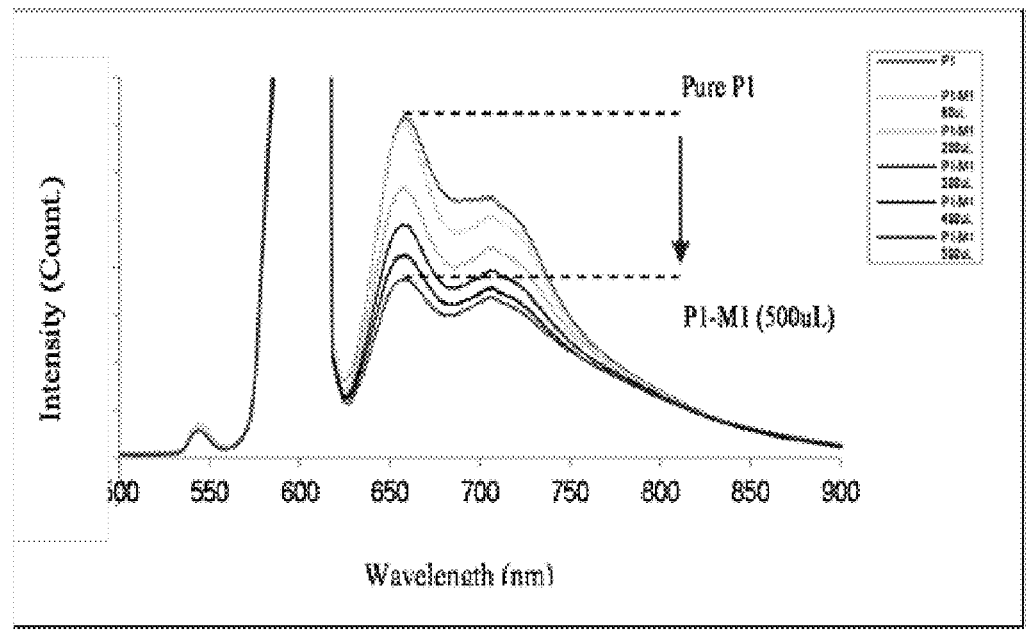
FIG. 29 is a graph illustrating progressive fluorescence turn-off by adding M1 to the P1 fluorescence solution, according to an embodiment of the present invention.

FIG. 29 shows the titration measurement results of the P1 in DMF (2 mL of $3\times10^{-4}$ mol/L P1 in DMF solution) when M1 was added progressively. By adding the proper amount of M1 (500 µL of 3.3 mg/mL M1 in DMF solution) the fluorescence was quenched as low as 53% of its maximum.

Figure 30:
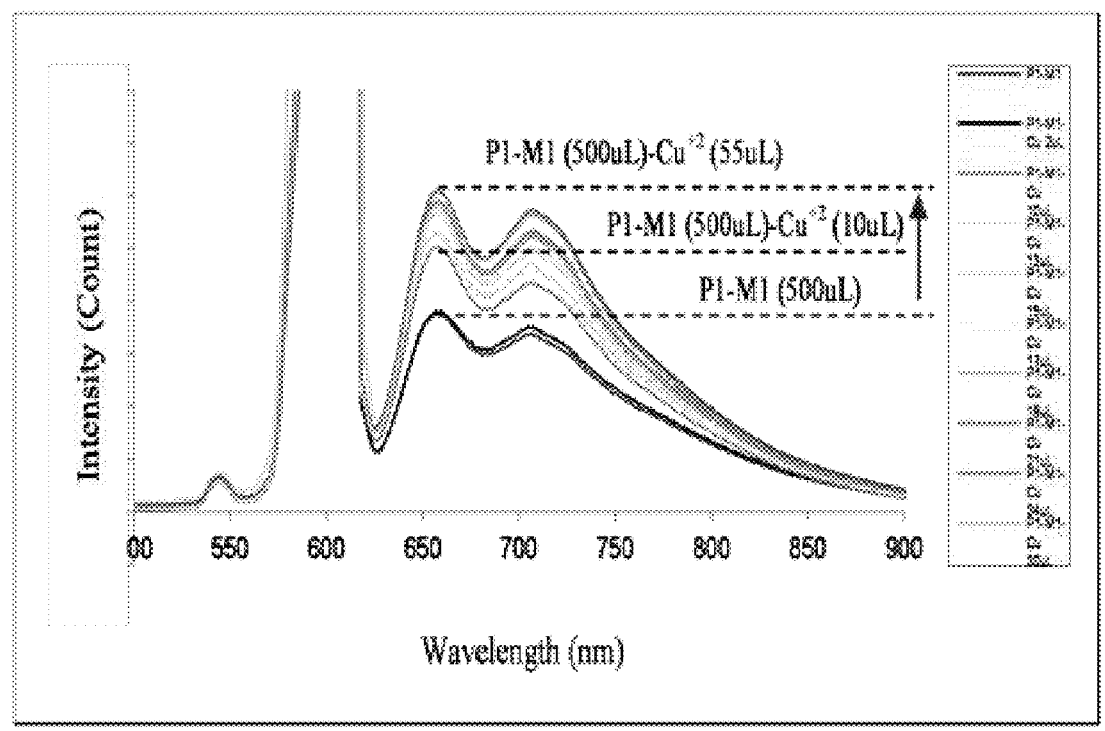
FIG. 30 is a graph illustrating progressive fluorescence turn-on by adding $Cu^{+2}$ to the P1-M1 quenched fluorescence solution, according to an embodiment of the present invention.

M1 also played a role of a highly selective receptor of $Cu^{+2}$. Absorbing of $Cu^{+2}$ by M1 would break the P1-M1 pair and the fluorescence was released again. The fluorescence signal was turned-on upon adding $Cu^{+2}$ to the P1-M1 solution so the whole process is called turn-on of the fluorescence as shown in FIG. 30. The high sensitivity of P1-M1 towards $Cu^{+2}$ was revealed by FIG. 30, indicating the changes in the fluorescence of P1 upon releasing the P1-M1 pair when progressively adding Cu+2 (10-55 µL of $2\times10^{-1}$ mol/L CuCl2 solution). The fluorescence intensity increased with the steady increase of the Cu+2 as low as 10 uL.

In conclusion, the fiber-optic fluorescence sensor could be a very sensitive probe for highly selective detection of $Cu^{+2}$. The expression obtained shows how the captured refracting fluorescence rays in the SUT excite the portion of tunneling and guided rays in the air-cladded segment. Then, using a mode mixer on the sidewall in the air-cladded segment, it becomes possible to scatter light and to excite lossless bound modes in the cladded segment of the fiber, propagating towards spectrometer.

Moreover, using evaluation of the performance of this sensing system for detection of $Cu^{+2}$ shows a satisfactory quality of the fluorescence spectrum captured from a polymer fluorophore (P1) with an extremely low quantum yield of 0.0065.

The spectrometer is shown in FIGS. 1, 5 and 17. The spectrometer is an apparatus comprising a detector adapted to receive a light signal and to generate an interpretable signal comprising information about the spectrum (intensity for a range of frequencies or any other equivalent measure). Light-receiving devices, such as lenses or mirrors, can be provided so that the light signal reaches the detector. The spectrometer then sends the generated signal to a computer for interpretation and analysis.

The computer which is in communication with the spectrometer. It comprises at least a memory for storing instructions and data (e.g., the signal received by the spectrometer), and a processor in communication with the memory for executing the instructions. The computer usually comprises a user interface (e.g., a display) and/or an input/output connector for communication (using wired or wireless connections) via a cable or a communication network to allow data to be transmitted to another local or remote computer.

While preferred embodiments have been described above and illustrated in the accompanying drawings, it will be evident to those skilled in the art that modifications may be made without departing from this disclosure. Such modifications are considered as possible variants comprised in the scope of the disclosure.

The invention claimed is:

1. A fiber-optic sensor for measuring a light signal from a fluorescible sample, the fiber-optic sensor comprising:
    an optical fiber comprising a core having a portion which is un-cladded on a side of the optical fiber, the un-cladded portion of the core forming a surface by which the light signal from the fluorescible sample is inputted, the un-cladded portion of the core being corrugated on the surface to form at least two gratings on the side surface of the un-cladded portion of the core, each grating
    comprising periodically longitudinally spaced-apart valleys on the surface of the un-cladded portion of the core and
    being longitudinally spaced apart from any other grating of the at least two gratings.

2. The fiber-optic sensor of claim 1, wherein the optical fiber is a large-core optical fiber thereby being highly multi-mode.

3. The fiber-optic sensor of claim 2, wherein each grating is configured to couple high-order modes to low-order modes.

4. The fiber-optic sensor of claim 3, wherein the light signal from the fluorescible sample comprises leaky modes, the grating converting the leaky modes into bound core modes that can propagate within a cladded segment of the optical fiber for eventual detection at a detection device provided at an end of the optical fiber.

5. The fiber-optic sensor of claim 4, wherein each grating is characterized by parameters comprising: a period between its valleys, a depth of its valleys and a length of its valleys; the parameters being adjusted for optimal mode-conversion of a given wavelength according to coupled-mode equations.

6. The fiber-optic sensor of claim 5, wherein the given wavelength for which mode conversion is optimized is about a peak wavelength of fluorescence of a heavy metal ion in a fluorophore solution.

7. The fiber-optic sensor of claim 6, wherein the heavy metal ion comprises $Pb^{2+}$, $Cu^{2+}$, and combinations thereof.

8. The fiber-optic sensor of claim 6, wherein the heavy metal ion comprises $Pb^{2+}$, $Cu^{2+}$, $Co^{2+}$, $Ni^{2+}$, $Zn^{2+}$, $Cd^{2+}$, $Hg^{2+}$, $Ca^{2+}$, $Mg^{2+}$, $Mn^{2+}$, $Fe^{3+}$, $K^+$, and combinations thereof.

9. The fiber-optic sensor of claim 1, wherein each one of the at least two grating has an azimuth about which its valleys are imprinted.

10. The fiber-optic sensor of claim 9, wherein the at least two gratings is two gratings.

11. The fiber-optic sensor of claim 10, wherein the azimuths of the two gratings are substantially the same.

12. The fiber-optic sensor of claim 10, wherein the azimuths of the two gratings are substantially different.

13. The fiber-optic sensor of claim 12, wherein the azimuths of the two gratings differ from about 90°.

14. A method of fabricating a fiber-optic sensor, the method comprising:
  un-cladding a segment of a core of an optical fiber to uncover a surface on a side of the core;
  providing an energetic beam;
  imprinting a plurality of gratings on the surface on the side of the core, comprising imprinting a plurality of valley on the surface of the core using the energetic beam;
  wherein between each imprinting of a valley, a relative displacement along a longitudinal axis of the optical fiber is performed between the optical fiber and the energetic beam, such that each valley is periodically longitudinally spaced-apart from any other valley belonging to a given grating; and
  wherein between each imprinting of a grating, a relative displacement along a longitudinal axis of the optical fiber is performed between the optical fiber and the energetic beam, such that each grating is longitudinally spaced-apart from any other grating.

15. The method of claim 14, further comprising between each imprinting of a grating, rotating the optical fiber with respect to its longitudinal axis, such that each grating is provided at an azimuth different from that of any other grating.

16. The method of claim 15, wherein the plurality of gratings comprises imprinting two gratings.

17. The method of claim 16, wherein rotating the optical fiber between each imprinting of a grating comprises rotating the optical fiber by about 90° with respect to its longitudinal axis between the imprinting of the two gratings.

18. The method of claim 14, wherein the energetic beam is a laser beam.

19. The method of claim 14, wherein the energetic beam is an infrared radiation.

20. The method of claim 14, wherein the energetic beam is a high energy radiation, the method further comprising applying weight on the optical fiber while providing the high energy radiation.

21. The method of claim 14, wherein imprinting each grating comprises imprinting a grating characterized by parameters comprising: a period between its valleys, a depth of its valleys and a length of its valleys; the parameters being adjusted for optimal mode-conversion of a given wavelength according to coupled-mode equations.

22. The method of claim 21, wherein the given wavelength for which mode conversion is optimized is a peak wavelength of fluorescence of a heavy metal ion in a fluorophore solution.

23. The method of claim 22, wherein the heavy metal ion comprises $Pb^{2+}$, $Cu^{2+}$, and combinations thereof.

24. The method of claim 22, wherein the heavy metal ion comprises $Pb^{2+}$, $Cu^{2+}$, $Co^{2+}$, $Ni^{2+}$, $Zn^{2+}$, $Cd^{2+}$, $Hg^{2+}$, $Ca^{2+}$, $Mg^{2+}$, $Mn^{2+}$, $Fe^{3+}$, $K^+$, and combinations thereof.

* * * * *